US005602010A

United States Patent [19]

Hauptmann et al.

[11] Patent Number: 5,602,010

[45] Date of Patent: Feb. 11, 1997

[54] DNA ENCODING EQUINE-GAMMA INTERFERON AND RECOMBINANT PRODUCTION OF EQUINE IFN-γ POLYPEPTIDES

[75] Inventors: Rudolf Hauptmann, Ebreichsdorf, Austria; Adolf Himmler, San Francisco, Calif.; Peter Swetly, Vienna, Austria

[73] Assignee: Boehringer Ingelheim International GmbH, Germany

[21] Appl. No.: 263,214

[22] Filed: Jun. 17, 1994

Related U.S. Application Data

[60] Continuation of Ser. No. 780,978, Oct. 23, 1991, abandoned, which is a division of Ser. No. 131,420, Dec. 10, 1987, abandoned.

[30] Foreign Application Priority Data

Dec. 10, 1986 [DE] Germany .......................... 36 42 096.4

[51] Int. Cl.[6] .......................... C12N 15/23; C12N 15/71; C12N 5/10; C12N 1/21

[52] U.S. Cl. .................................... 435/69.51; 536/23.52; 536/24.31; 536/24.1; 435/252.3; 435/252.33; 435/254.11; 435/320.1; 435/325; 530/351; 424/85.5

[58] Field of Search ............................... 536/23.52, 24.1, 536/24.2, 24.31; 435/69.51, 320.1, 252.3, 240.2, 252.33, 254.11; 424/85.5

[56] References Cited

U.S. PATENT DOCUMENTS

| | | | |
|---|---|---|---|
| 4,656,131 | 4/1987 | Kitano et al. | 435/69.51 |
| 4,666,865 | 5/1987 | Chang et al. . | |
| 4,689,224 | 8/1987 | Bull et al. | 424/233.1 |
| 4,832,959 | 5/1989 | Engels et al. . | |
| 4,908,432 | 3/1990 | Yip . | |
| 4,917,887 | 4/1990 | Hauptmann et al. | 424/85.7 |

FOREIGN PATENT DOCUMENTS

| | | |
|---|---|---|
| 0036776 | 9/1981 | European Pat. Off. . |
| 0088622 | 9/1983 | European Pat. Off. . |
| 0088540 | 9/1983 | European Pat. Off. . |
| 0115613 | 8/1984 | European Pat. Off. . |
| 0161504 | 11/1985 | European Pat. Off. . |
| 0186098 | 7/1986 | European Pat. Off. . |
| 0254593 | 1/1988 | European Pat. Off. . |

OTHER PUBLICATIONS

Yilma, T. (1986) *Meth. Enzymol.* 119:130–136, "Induction of Equine Interferons".

English language abstract for European Patent Publication No. EP 0 186 098 (Ref. AO1), Derwent WPI Accession No. 86–170649/27.

English language abstract for European Patent Publication No. EP 0 115 613 (Ref. AP1), Derwent WPI Accession No. 84–165768/27.

English language abstract for European Patent Publication No. EP 0 161 504 (Ref. AL2), Derwent WPI Accession No. 85–277157/45.

Gray, P. W., and Goeddel, D. V., "Cloning and Expression of Murine Immune Interferon cDNA," *Proc. Natl. Acad. Sci. USA* 80:5842–5846 (1983).

Gray, P. W. and Goeddel, D. V., "Structure of the Human Immune Interferon Gene," *Nature* 298:859–863 (1982).

Dijkema, R., et al., "Cloning and Expression of the Chromosomal Immune Interferon Gene of the Rat," *EMBO J.* 4(3):761–767 (1985).

Cerretti, D. P., et al., "Cloning, Sequence, and Expression of Bovine Interferon–γ," *J. Immunol.* 136:4561–4564 (1986).

Yilma, T., et al., "Preliminary Characterization of Equine Interferons and their Antiviral Activities on Bovine, Ovine, and Human Cells," *J. Interferon Res.* 2(3):363–370 (1982).

Copy of the European Search Report for the corresponding European Patent Application, EPO Application No. 87118264, EPO Publication No. 0 271 824.

Rubin, B.Y., et al., "The Anticellular and Protein–Inducing Activities of Human γ Interferon Preparations Are Mediated by the Interferon," *J. Immunol.* 130:1019–1020 (1983).

Kearney, J. F., "Chapter 28. Hybridomas and Monoclonal Antibodies," in: *Fundamental Immunology*, Paul, W. E., ed., New York: Raven Press, pp. 751–766 (1984).

Buell, G., et al. (1985) *Nucl. Acids Res.* 13(6):1923–38.

Matsumura, P., et al. (1984) *J. Bacteriol.* 160(1):36–41.

Wilson et al. *J. Mol. Biol* 166:457–475 (1983).

Edington et al. *J. Interferon Res* 9(4):385–388 (1989).

Shaw et al. *Nucleic Acids Res* 11(3):555–573 (1983).

*Primary Examiner*—David L. Fitzgerald
*Attorney, Agent, or Firm*—Sterne, Kessler, Goldstein & Fox P.L.L.C.

[57] ABSTRACT

The present invention relates to a process for preparing horse interferon-gamma (equine interferon gamma, EqIFN-γ, DNA sequences which encode this polypeptide, suitable vectors and host organisms containing these DNA sequences and the EqIFN-γ itself. The invention further relates to partial DNA sequences which encode polypeptides which differ structurally from the natural EqIFN-γ polypeptide. The use of the proteins is also described.

21 Claims, 11 Drawing Sheets

EqIFN-gamma    (Lambda Eq - 2 Bam HI-fragment)

```
                                                                   GGATC      5
CCACAAGAATGGCACGGGTGGGCATAATGGGTCTGTCTCATCGTCAAAAGACCCAAGGAG               65
TTGAAAGGAAACTCTAACTACAACACCAAAATGCCACAAAACCATAGTTATTAATACAAA              125
CTAACTAGCATCTGTGCCTATCTGTCACCATCTCATCTGAAAAAACTTGTGAAAATACGT              185
AATCCTGATGAGACTTCAATTAGGTATAAAAACCAGCCCCAGAAGGCGAGGCAGTACACT              245
CTTCTGATCGCCGGTAGGGCAGCTATTAGAAAAGAAAGATCAGCTGAGGCCTTGGGACCT              305
GATCAGCTTAGTACAGAAGTGACTGCTTTCAACTACTTAGGCCTAACTCTCTCCGAAACA              365
```

```
 -20                -15                 -10
 Met Asn Tyr Thr Ser Phe Ile Leu Ala Phe Gln Leu Cys Ala Ile
 ATG AAT TAT ACA AGT TTT ATC TTG GCT TTT CAG CTG TGT GCG ATT              410
  -5                 -1  1                 5                  10
 Leu Gly Ser Ser Thr Tyr Tyr Cys Gln Ala Ala Phe Phe Lys Glu
 TTG GGT TCT TCT ACC TAT TAC TGC CAG GCC GCG TTT TTT AAA GAA              455
                         15
 Ile Glu Asn Leu Lys Glu Tyr Phe
 ATA GAA AAC CTA AAG GAA TAT TTT GTAAGTATGACCTTTTAATAATACTTAC             507
```

```
     I N T R O N  1
TTGTGGTTGAAATGACTGAACGTTGTCTTGGAGTTGGATCTCTGATAGGCTGTCCTCTCT              567
ACTCCACAGTCATCTTGAGAAGACTGGGTGTTATTTTCTCTGTTTGTTGACTGGATGAGT              627
TTTTCTTTTTTTTACTAAATGATCTAGATATTGCTTTAACCCTCTGCTCAATTTGCTATA              687
GAGACTTAGAGAGGGTTCATGAATCTTCCAAAAGATGGGCTTAACAGGTTTATAAAGCAT              747
AGTGAAGTTGACAATTTTGTGGTGAGAAGCCACTGAATTGTGATAAGTCAAGTAGTGTGG              807
ACATTGAAAAAATGACTAGCTATTAGTTTCTAACTTCTCAGGTTACTATGATGGTGACAA              867
TAAAAGGTCAAGATTAGCATTAAAATGGTAATCTGAAATAATTGATCAGTTAAAGAAGGC              927
GCTGTCCTGAAAGGTTTGGCTGAAAAAAAATCACTTTCAGGTGTTTTCCTCCAAAAAATG              987
ATTTTAAAATCTTACTGCCCCGTTTGTGTTAGCTGTGAAGTACTCTGGAACTCAGTCAAT             1047
TGCTGAGATTTTGTACGAGTTATAAGCTGGCTTATATTTAAAAAATTTTTTTGTTTTTGT             1107
TTTATGAGTTTCTTTTAAAATGTTATTTATGGTTAATTAAAATAGTTTTTGCATTTTAAA             1167
TATTTTATTATTTGTCCAAAATTTAGCTATTTTAATTATAGTTCGAGCTCTCTTTTAGAG             1227
CTGACATAAGACCATAGGGGAGGCACAGATAGATGTGATGGAGCCCTGTACCAGACGGGG             1287
GCAGTATCTTATAGTGGGTTGCCTTTGCTGATCTTTTTACTAGACTTGAAATTATTTGCT             1347
TTTCCTTCCTATGGTTATTTGGGACTATTGAAGTATCACCAGCCCTGTTGAGTTCATCTG             1407
TAATATTGTAATTCAAGGGTTACACTAGAAAATAAGAAAGCTAAAACAGCACGATAATCT             1467
TTGGCTACATCCAACACAATAGCTTTTGGGAATACTTATTGTTAGAACTAAACAGAGGGT             1527
TGAAAAGAAAATCAGTGAATACTGTCAGCATCTGAGTTCAATAAAACGTGAAGTACATTT             1587
                                                                         20
                                                                     Asn Ala
TTAGGGCAATTCATGGACTAATTGTAAACCAAGTTTTCCTTCCTTTTTCAG AAC GCA             1644
             25                 30                  35
Arg Asn Pro Asp Val Gly Asp Gly Gly Pro Leu Phe Leu Asp Ile
AGA AAC CCA GAT GTA GGG GAT GGT GGG CCT CTT TTC CTG GAT ATC             1689
```

FIG. 1A

```
                  40                            I N T R O N 2
Leu Lys Asn Trp Lys Glu
TTG AAG AAC TGG AAA GAG GTAAGCTAAGTATTTCCATTTGGTTGATTTTCCTGT    1743
TGCTTATTTTCTGGTGGATGAATTCACACCAACCTCTCTTTGTGCTCTTTTCTCCCTAG     1802

                45                  50                  55
Asp Ser Asp Lys Lys Ile Ile Gln Ser Gln Ile Val Ser Phe Tyr
GAT AGT GAC AAA AAA ATA ATT CAG AGC CAA ATC GTC TCC TTC TAC     1847

                60                  65                  70
Phe Lys Leu Phe Glu Asn Leu Lys Asp Asn Gln Val Ile Gln Lys
TTC AAA CTC TTT GAA AAC TTG AAA GAT AAC CAG GTC ATT CAA AAG     1892

                75                  80                  85
Ser Met Asp Thr Ile Lys Glu Asp Leu Phe Val Lys Phe Phe Asn
AGC ATG GAC ACC ATC AAG GAG GAC CTG TTC GTT AAG TTC TTT AAC     1937

                90                  95                  100
Ser Ser Thr Ser Lys Leu Glu Asp Phe Gln Lys Leu Ile Gln Ile
AGC AGC ACC AGC AAG CTG GAA GAC TTC CAA AAG CTG ATT CAG ATT     1982

                  I N T R O N
Pro
CCG GTGAGGAGATCTTAATTCTTTCTTTGGTTTCATTACAGAGGTTCTTGCAAAGTGCT    2041
TACGTCCCAGAAAGTAGAAATGAACTATGAAATGAACCCGTGGCCAAAACTCCTCCTTCC    2101
TAATTCCATTTGTGCTTTGAGAGACTTTGCTAAGTCAGTATGGGAATCATTTAAATTTGT    2161
GATTTGGGGAAATGCTGGCACTATGACTACTGCACAAAGGCAGGTGAAGGGACAAATCCA    2221
GTGAGGAGGGGGCAGTGAAGAAGTGGAGGGGAGTCTGGAGAAGCAGGTCTCTCCTTGCCC    2281
CTTGTTCGTGAGATGAAATCCTCCTGCTTTGGATGGGAGGCTGCGTGTCTTGGTGGAAAG    2341
AGCAGTGGGAGGAGGGAGAAGATTTGTGCTCCTCCCAGCTCAGCCACCAAGAAACTGTGA    2401
CCTCAGATGAATCACAGGCCTGGCTGGGGCTCAGTTTCCTCATCTTAAAAGAGGCCTATT    2461
GGGTTCACTAAAATTTCTATGATCTTCTTTGCTCTATAATCCTACAATTCTGTGGACAGA    2521
AAATGAAATGAGGTAGGAGAAAGAAATAGCCTTTGAAGAGGTTCTTGGGCATTCCACTGC    2581
CAGGCTCTGGTCAACCTTCATACTCTGCAGCCCAAGAAGAGGCAAGACCATTTGTCTGTT    2641
TTTGGAAATGCAAATAGGCGGCATTTATACCTCACGAAAGAACTGTTCTGTCAACTTTTG    2701
GATACTGGGCTATCTTGGCTGGAGAAATCCTTAGGCTCCCAAACTTTCTCTCATGAAATT    2761
GTCTTGAGTCTTTAAATTTATGGCTTCTCGAAGCTGAGAGATAACTTTAAGCATAAAGAC    2821
AAATTACATTTTCCAACATTTTGTCTAAGAGACAAAGACCTCCACATGCCTTTGGGTTTG    2881
GCCTGGATCTAAATGGGCTTGAATGAGAAGGGGAGGGTGTTGTTATGACTATGTTTAGAA    2941
GAGAAAACAGAGGTTTGGAGAGGTTAAGTGGCTGGTTCAAAGTCAGAGTTATTGCACACA    3001
CAGGATTCGAACCCATATGTTTTGTCCCTCCACTTTAGGGTTCTTTTCGCTACATAATTT    3061
TGAGAATTCTGTACCAGTCAATTTAAGGATGTGTGATGTTCCCCATCCTATTACAGCACA    3121
ACCAGCAATTTAATTATAATTTTAGTCTTAACTGCTGAAGAAAGCAGCATTACATATTAA    3181
GCTAACATATTCCTGGTGAAAGCAACTTTTTCAAAGGAATATTTCTATTTTCATGGACCA    3241
TGACAGTAGCACAGCCTGATGGCTTGTATGCCTGAAACTAATTTTGCTGTTTTCTTTCCC    3301
```

FIG. 1B

```
                 105                 110                     115
      Val Asn Asp Leu Lys Val Gln Arg Lys Ala Ile Ser Glu Leu
AATAG GTA AAT GAT CTG AAG GTC CAG CGC AAA GCA ATA AGT GAA CTC    3348
             120                 125                 130
Ile Lys Val Met Asn Asp Leu Ser Pro Lys Ala Asn Leu Arg Lys
ATC AAA GTG ATG AAT GAT CTG TCG CCC AAA GCT AAC CTG AGG AAG      3393
             135                 140                 145
Arg Lys Arg Ser Gln Asn Pro Phe Arg Gly Arg Arg Ala Leu Gln
CGG AAG AGG AGT CAG AAT CCA TTT CGA GGC CGG AGA GCG TTG CAA      3438

***
TAG TGGTCATCCTGCCTGCAATATTTGAATTTTTAAATCTAAATCTATTTATTAATATT    3497
TAATATTTTACATTATTTATATGGGGAATATATTTTTAAACTCATCAAAGTATTTATAAT    3557
AGCAACTTTTATGTAATGAAAATGGGTATCTATTAATATATATATTATTTATAATTCCTG    3617
TATGGTGTGACTATTTCACTTGACCCTTTTTTTTCTGACCAACTAGGCAAGATTATGTGA    3677
TTACAAGGCTTTAACTCAGGGGCCAACTAGGGAGTGGGTAGCCGACCTACCAAGACCCTG    3737
TGAGCTGTGTGTTTATTTCCCTCAATGATACAATGAACACTTATAAAGGAAAGGAGGGCC    3797
TCCAGTCACTGCCTGTTGGAGAACATGTCTGCATTGTGAGCCACTGCTTAATGGCATGTC    3857
AAACCACGCTTGAATGTGTCAGATGATAGGGCTTGTCCCCTGATAAAGCTTAGTATCTCC    3917
TCTCATGCCTAGTGCTTCAGAATATTGTTGACAACTGTGACTGCACCCAAATGGAAAGTA    3977
ATTTATTTGTTTAGTTTACCAATATTTAATAAATATGAATAAAGTATAATTTCATAACTA    4037
TTTATGCTGCGTCCGGCTTTTTCTAAGTGAGGACTGGGGTAAATGAACTACAAACTAATG    4097
AATCAGTAAGAGGGAACTCGTTTTTAGCGGTGGAAATCTTAGCTGGATTAAGCCCCATGA    4157
AACGTGGTATTTCTCTCCACTGGAGATTTGTTGGCTACTACTCCTCCATGTAGCAGCTCT    4217
TTATCTTTCCAAAATATAAATTTAATTATGTCACCATTTACTTCAGAGCTTCTGCGATGG    4277
AAAGTAGTTCAAATAGTTTAGCTTAGCACACAAAGCTTTGTTTCTCCCTCCTCCCTCAAC    4337
TCTGCACTGTGCTCTTCATCTTGGTGTCCCCACGTCCTCTGTCCACTTCGGGCAAACCAC    4397
CGGGAATGTCATGGTGAGGGTGAGCTCTAGGGAGAGAGGGCTGGATTAGAATTTCGGCCC    4457
CACCATTACCAGTAGTATGACCTTTAATGAATTACTTGTATTCTCTAAGCTCCAGTTTCC    4517
TCATCTGACACAAGAGAATAATTGTGCCTAAAATTGTGGTGAGAGTTTGTTCTTTCACTC    4577
AAGAAGTGTTTACTGGAGCATCCACTAGTTGCCTAGTGCTGTTCTAGGCACTTGAGATAC    4637
ATTTGTGAACAAAATAGTCAAGGATCC                                     4664
```

FIG. 1C

GAMMA-INTERFERON

```
           S1        S10           S20  1         10           20           30         40         50         60         70
           |         |             |    |         |            |            |          |          |          |          |
HUMAN      MKYTSYILAFQLCIVLGSLG  CYCQDPYVKE  AENLKKYFNA  GHSDVADNGT LFLGILKNWK EESDRKIMQS QIVSFYFKLF KNFKDDQSIQ
EQUINE     MNYTSFILAFQLCAILGSST  YYCQAAFFKE  IENLKEYFNA  RNPDVGDGGP LFLDILKNWK EDSDKKIIQS QIVSFYFKLF ENLKDNQVIQ
BOVINE     MKYTSYFLALLLCGLLGFSG  SYGQGQFFRE  IENLKEYFNA  SSPDVAKGGP LFSDILKNWK DESDKKIIQS QIVSFYFKLF ENLKDNQVIQ
MURINE     MNATHCILALQLFLMAV-SG  CYCHGTVIES  LESLNNYFNS  SGIDV-EEKS LFLDIWRNWQ KDGDMKILQS QIISFYLRLF EVLKDNQAIS
RAT        MSATRRVLVLQLCLMAL-SG  CYCQGTLIES  LESLKNYFNS  SSMDAMEGKS LLLDIWRNWQ KDGNTKILES QIISFYLRLF EVLKDNQAIS

CONSENSUS  M--T---La--Lc-----sg  -Ycq------  -E-Lk-YFN-  ---Dv----- LfldI--NW- ---d-KI-qS QI-SFY--LF e-lKDnQ-I-


               80         90         100        110        120        130        140        150
               |          |          |          |          |          |          |          |
HUMAN      KSVETIKEDM NVKFFNSNKK KRDDFEKLTN YSVTDLNVQR KAIHELIQVM AELSPAAKTG KRKRSQMLFR GRRAFQ
EQUINE     KSMDTIKEDL FVKFFNSSTS KLEDFQKLIQ IPVNDLKVQR KAISELIKVM NDLSPKANLR KRKRSQNPFR GRRALQ
BOVINE     RSMDIIKQDM FQKFLNGSSE KLEDFKKLIQ IPVDDLQIQR KAINELIKVM NDLSPKSNLR KRKRSQNLFR GRRASM
MURINE     NNISVIESHL ITTFFSNSKA KKDAFMSIAK FEVNNPQVQR QAFNELIRVV HQLLPESSLR KRKRSRC
RAT        NNISVIESHL ITNFFSNSKA KKDAFMSIAK FEVNNPQIQH KAVNELIRVI HQLSPESSLR KRKRSRC

CONSENSUS  -----I---- ---Ff--s-- K---F----- --V-----Qr kA--ELI-V- --LsP---lr KRKRS---FR GRRA--
```

FIG. 2

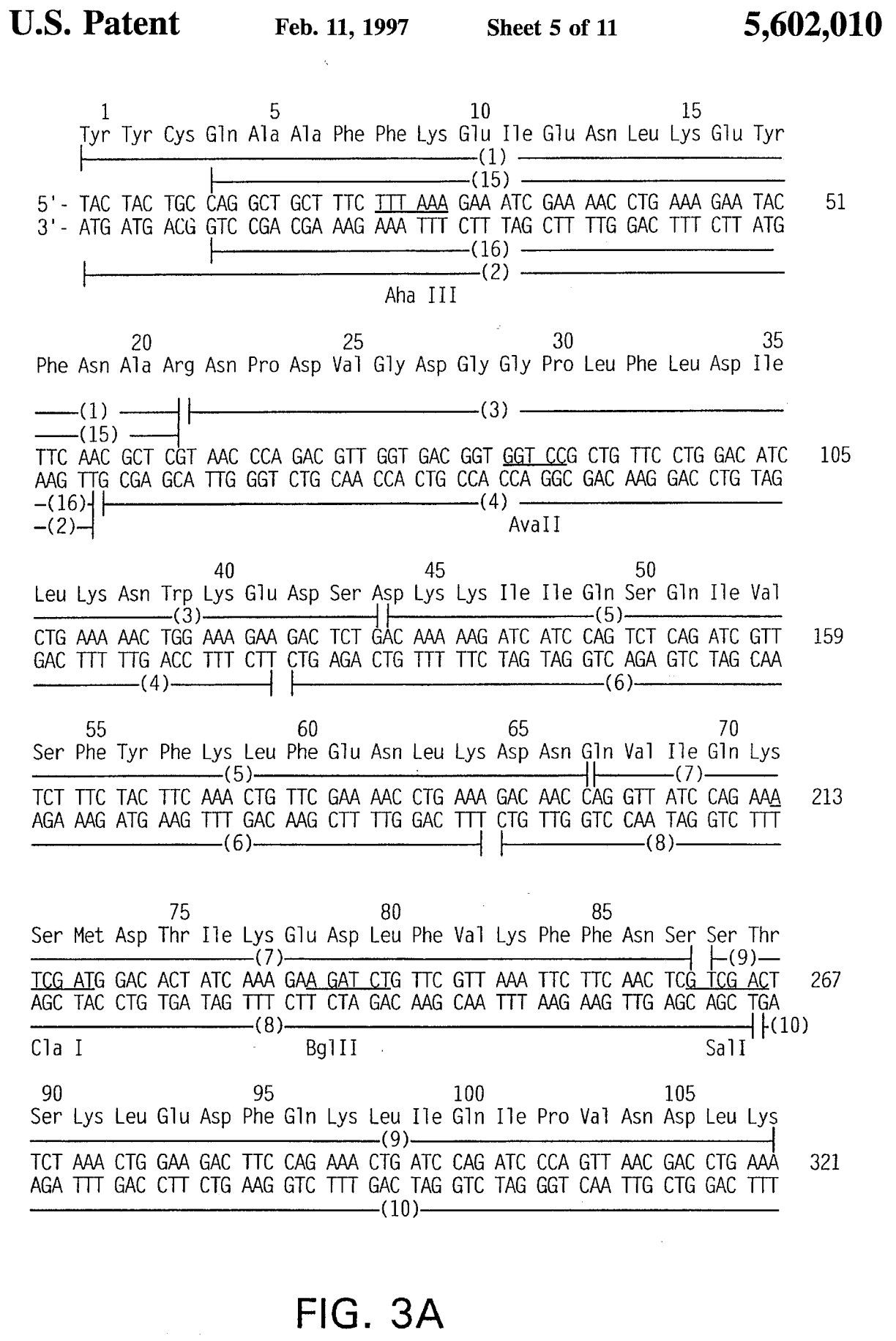

```
1                5                   10                  15
Tyr Tyr Cys Gln Ala Ala Phe Phe Lys Glu Ile Glu Asn Leu Lys Glu Tyr
(1)
(15)
5'- TAC TAC TGC CAG GCT GCT TTC TTT AAA GAA ATC GAA AAC CTG AAA GAA TAC   51
3'- ATG ATG ACG GTC CGA CGA AAG AAA TTT CTT TAG CTT TTG GAC TTT CTT ATG
(16)
(2)
Aha III

    20                  25                  30                  35
Phe Asn Ala Arg Asn Pro Asp Val Gly Asp Gly Gly Pro Leu Phe Leu Asp Ile
(1) (3)
(15)
TTC AAC GCT CGT AAC CCA GAC GTT GGT GAC GGT GGT CCG CTG TTC CTG GAC ATC   105
AAG TTG CGA GCA TTG GGT CTG CAA CCA CTG CCA CCA GGC GAC AAG GAC CTG TAG
(16) (4)
(2)
AvaII

            40                  45                  50
Leu Lys Asn Trp Lys Glu Asp Ser Asp Lys Lys Ile Ile Gln Ser Gln Ile Val
(3) (5)
CTG AAA AAC TGG AAA GAA GAC TCT GAC AAA AAG ATC ATC CAG TCT CAG ATC GTT   159
GAC TTT TTG ACC TTT CTT CTG AGA CTG TTT TTC TAG TAG GTC AGA GTC TAG CAA
(4) (6)

    55                  60                  65                  70
Ser Phe Tyr Phe Lys Leu Phe Glu Asn Leu Lys Asp Asn Gln Val Ile Gln Lys
(5) (7)
TCT TTC TAC TTC AAA CTG TTC GAA AAC CTG AAA GAC AAC CAG GTT ATC CAG AAA   213
AGA AAG ATG AAG TTT GAC AAG CTT TTG GAC TTT CTG TTG GTC CAA TAG GTC TTT
(6) (8)

            75                  80                  85
Ser Met Asp Thr Ile Lys Glu Asp Leu Phe Val Lys Phe Phe Asn Ser Ser Thr
(7) (9)
TCG ATG GAC ACT ATC AAA GAA GAT CTG TTC GTT AAA TTC TTC AAC TCG TCG ACT   267
AGC TAC CTG TGA TAG TTT CTT CTA GAC AAG CAA TTT AAG AAG TTG AGC AGC TGA
(8) (10)
Cla I                 BglII                                   SalI

90                  95                  100                 105
Ser Lys Leu Glu Asp Phe Gln Lys Leu Ile Gln Ile Pro Val Asn Asp Leu Lys
(9)
TCT AAA CTG GAA GAC TTC CAG AAA CTG ATC CAG ATC CCA GTT AAC GAC CTG AAA   321
AGA TTT GAC CTT CTG AAG GTC TTT GAC TAG GTC TAG GGT CAA TTG CTG GAC TTT
(10)
```

FIG. 3A

```
            110                 115                 120                 125
Val Gln Arg Lys Ala Ile Ser Glu Leu Ile Lys Val Met Asn Asp Leu Ser Pro
|--------------------------------------(11)--------------------------------
GTT CAG CGT AAG GCT ATC TCT GAA CTG ATC AAA GTT ATG AAC GAC CTG TCT CCA     375
CAA GTC GCA TTC CGA TAG AGA CTT GAC TAG TTT CAA TAC TTG CTG GAC AGA GGT
--(10)--||-----------------------------(12)--------------------------------

                130                 135                 140
Lys Ala Asn Leu Arg Lys Arg Lys Arg Ser Gln Asn Pro Phe Arg Gly Arg Arg
--(11)--||-------------------------------------(13)-----------------------
AAA GCT AAC CTG CGT AAA CGT AAA CGT TCT CAG AAC CCA TTC CGT GGT CGT CGT     429
TTT CGA TTG GAC GCA TTT GCA TTT GCA AGA GTC TTG GGT AAG GCA CCA GCA GCA
--(12)------------||---------------------------(14)-----------------------

    145
Ala Leu Gln ***
------(13)------|
GCT CTT CAG TAA G        -3'                                                442
CGA GAA GTC ATT CCTAG    -5'                                                446
------(14)----------|
                BamHI
```

FIG. 3B

```
       1               5                   10                  15
      Tyr Tyr Cys Gln Ala Ala Phe Phe Lys Glu Ile Glu Asn Leu Lys Glu Tyr Phe
eq    TAT TAC TGC CAG GCC GCG TTT TTT AAA GAA ATA GAA AAC CTA AAG GAA TAT TTT
        *               *   *   *               *           *   *       *   *
syn   TAC TAC TGC CAG GCT GCT TTC TTT AAA GAA ATC GAA AAC CTG AAA GAA TAC TTC

           20                  25                  30                  35
      Asn Ala Arg Asn Pro Asp Val Gly Asp Gly Gly Pro Leu Phe Leu Asp Ile Leu
eq    AAC GCA AGA AAC CCA GAT GTA GGG GAT GGT GGG CCT CTT TTC CTG GAT ATC TTG
            * * *           *   *   *   *       *   *   *           *     *
syn   AAC GCT CGT AAC CCA GAC GTT GGT GAC GGT GGT CCG CTG TTC CTG GAC ATC CTG

                   40                  45                  50
      Lys Asn Trp Lys Glu Asp Ser Asp Lys Lys Ile Ile Gln Ser Gln Ile Val Ser
eq    AAG AAC TGG AAA GAG GAT AGT GAC AAA AAA ATA ATT CAG AGC CAA ATC GTC TCC
        *               *   * **        *   *   *         ***   *       *   *
syn   AAA AAC TGG AAA GAA GAC TCT GAC AAA AAG ATC ATC CAG TCT CAG ATC GTT TCT

       55                  60                  65                  70
      Phe Tyr Phe Lys Leu Phe Glu Asn Leu Lys Asp Asn Gln Val Ile Gln Lys Ser
eq    TTC TAC TTC AAA CTC TTT GAA AAC TTG AAA GAT AAC CAG GTC ATT CAA AAG AGC
                        *   *         *         *           *   *   *   * ***
syn   TTC TAC TTC AAA CTG TTC GAA AAC CTG AAA GAC AAC CAG GTT ATC CAG AAA TCG

               75                  80                  85                  90
      Met Asp Thr Ile Lys Glu Asp Leu Phe Val Lys Phe Phe Asn Ser Ser Thr Ser
eq    ATG GAC ACC ATC AAG GAG GAC CTG TTC GTT AAG TTC TTT AAC AGC AGC ACC AGC
                *       *   *   *               *       *     *** ***   * ***
syn   ATG GAC ACT ATC AAA GAA GAT CTG TTC GTT AAA TTC TTC AAC TCG TCG ACT TCT

                       95                  100                 105
      Lys Leu Glu Asp Phe Gln Lys Leu Ile Gln Ile Pro Val Asn Asp Leu Lys Val
eq    AAG CTG GAA GAC TTC CAA AAG CTG ATT CAG ATT CCG GTA AAT GAT CTG AAG GTC
        *                   *   *       *       *   *   *   *   *       *   *
syn   AAA CTG GAA GAC TTC CAG AAA CTG ATC CAG ATC CCA GTT AAC GAC CTG AAA GTT

           110                 115                 120                 125
      Gln Arg Lys Ala Ile Ser Glu Leu Ile Lys Val Met Asn Asp Leu Ser Pro Lys
eq    CAG CGC AAA GCA ATA AGT GAA CTC ATC AAA GTG ATG AAT GAT CTG TCG CCC AAA
            *   *   *   * **        *           *       *   *       *   *
syn   CAG CGT AAG GCT ATC TCT GAA CTG ATC AAA GTT ATG AAC GAC CTG TCT CCA AAA
```

FIG. 4A

```
                 130                 135                 140
     Ala Asn Leu Arg Lys Arg Lys Arg Ser Gln Asn Pro Phe Arg Gly Arg Arg Ala
eq   GCT AAC CTG AGG AAG CGG AAG AGG AGT CAG AAT CCA TTT CGA GGC CGG AGA GCG
                 * *   *   *   * * **          *       *   *   *   * *   *
syn  GCT AAC CTG CGT AAA CGT AAA CGT TCT CAG AAC CCA TTC CGT GGT CGT CGT GCT

     145
     Leu Gln ***
eq   TTG CAA TAG
     * *   *   *
syn  CTT CAG TAA
```

FIG. 4B

Codons used for mature EqIFN-gamma: natural gene (synthetic gene)

| | T | C | A | G | |
|---|---|---|---|---|---|
| T | 6 ( 1) Phe | 0 (7) Ser | 2 ( 0) Tyr | 0 (0) Cys | T |
| | 6 (11) Phe | 1 (0) Ser | 2 ( 4) Tyr | 1 (1) Cys | C |
| | 0 ( 0) Leu | 0 (0) Ser | 0 ( 1) STOP | 0 (0) STOP | A |
| | 3 ( 0) Leu | 1 (3) Ser | 1 ( 0) STOP | 1 (1) Trp | G |
| C | 1 ( 1) Leu | 1 (0) Pro | 0 ( 0) His | 0 (8) Arg | T |
| | 2 ( 0) Leu | 1 (0) Pro | 0 ( 0) His | 1 (0) Arg | C |
| | 1 ( 0) Leu | 2 (4) Pro | 4 ( 0) Gln | 1 (0) Arg | A |
| | 7 (13) Leu | 1 (1) Pro | 6 (10) Gln | 2 (0) Arg | G |
| A | 4 ( 0) Ile | 0 (2) Thr | 3 ( 0) Asn | 3 (0) Ser | T |
| | 4 (11) Ile | 2 (0) Thr | 8 (11) Asn | 5 (0) Ser | C |
| | 3 ( 0) Ile | 0 (0) Thr | 9 (17) Lys | 2 (0) Arg | A |
| | 2 ( 2) Met | 0 (0) Thr | 10 ( 2) Lys | 2 (0) Arg | G |
| G | 1 ( 7) Val | 1 (6) Ala | 7 ( 1) Asp | 1 (4) Gly | T |
| | 3 ( 0) Val | 1 (0) Ala | 4 (10) Asp | 1 (0) Gly | C |
| | 2 ( 0) Val | 2 (0) Ala | 6 ( 8) Glu | 0 (0) Gly | A |
| | 1 ( 0) Val | 2 (0) Ala | 2 ( 0) Glu | 2 (0) Gly | G |

FIG. 5

DNA ENCODING EQUINE-GAMMA INTERFERON AND RECOMBINANT PRODUCTION OF EQUINE IFN-γ POLYPEPTIDES

This application is a continuation of application Ser. No. 07/780,978, filed 23 Oct. 1991 and now abandoned, which is in turn a divisional of application Ser. No. 07/131,420, filed 10 Dec. 1987, also now abandoned.

This invention relates to a process for preparing horse gamma interferon (equine interferon-gamma, EqIFN-γ) DNA sequences which encodes polypeptide, suitable vectors and host organisms containing these DNA sequences and EqIFN-γ itself. The invention further relates to partial DNA sequences which encodes polypeptides which differ structurally from natural EqIFN-γ polypeptide. The use of the proteins is also described.

DESCRIPTION OF THE BACKGROUND ART

Interferons are proteins which are secreted by eukaryotic cells after virus infections or other stimulations and may in turn protect the cells from virus infections. Three classes of interferons are known at present: they are referred to as interferon-α, interferon-β and interferon-γ (abbreviated to IFN-α, IFN-β and IFN-γ). They differ in their structure and effects. Thus, interferons may have a regulating effect on the cells of the immune system or they may also influence the differentiation of cells and the growth of tumours.

In 1965 F. Wheelock discovered a polypeptide which protected certain cells from virus infections (Science 149, 310 (1965). Polypeptides with these properties are referred to as immune interferon, type II interferon, interferon-gamma or IFN-γ, although they are polypeptides belonging to the class of the lymphokines. In addition to human interferon-γ, bovine, murine and rat interferon-γ have also become known. All the γ-interferons known hitherto occur in glycosylated form, although the glycosylation has no influence on the biological activity (Keller et al., J. Biol. Chem. 258, 8010 (1983)).

For a long time, it had been assumed that interferons had a species-specific activity. In vitro tests, however, showed that IFN preparations from cattle could trigger an antiviral activity in monkeys and humans (Tovey, M. G. et al. J. Gen.

Virol. 36, 341–344 (1977). This species interactivity might possibly be connected with the more or less great homology of the genes or proteins: it has not been possible to test this assumption owing to the small amounts of animal interferons.

In spite of the species interactivities detected, side-effects such as antigenicity are observed when interferons from different species are used and these are unacceptable in therapy.

Since, however, animal husbandry and the keeping of domestic pets have considerable economic importance, there is a need for interferons for various species which can be used by veterinary surgeons.

Highly purified animal interferon of various species would moreover offer the welcome opportunity of investigating the mechanisms of activity for interferons in order to arrive at models which could be transferred to man.

The first investigations with animal interferons were carried out using preparations from natural cell material; the yield and purity of the interferons prepared by this method make them unsuitable for the preparation of drugs.

By developing the recombinant DNA technique it is possible to produce heterologous proteins from microorganisms. In this way, for example, human interferons (Hu-IFN) have been prepared and most recently various non-human inter ferons have also been obtained.

DESCRIPTION OF THE PREFERRED EMBODIMENTS

One aim of this invention was to prepare equine γ-interferons by genetic engineering and to prepare the DNA sequences required for it.

This aim was achieved according to the invention by using the so-called probe technique. The probe used was a DNA sequence known from the literature, derived from human γ-interferon (Gray and Goeddel; Nature 298, 859–863 (1982)).

However, partial or complete sequences of other γ-interferons are also suitable as probes. The starting material for the search was a DNA library obtained from normal horse liver tissue. In this way, the gene coding for EqIFN-γ with the flanking regions of formula I as follows has been isolated for the first time:

```
                                                                GGATC        5    Formula I

CCACAAGAATGGCACGGGTGGGCATAATGGGTCTGTCTCATCGTCAAAAGACCCAAGGAG    65

TTGAAAGGAAACTCTAACTACAACACCAAAATGCCACAAAACCATAGTTATTAATACAAA   125

CTAACTAGCATCTGTGCCTATCTGTCACCATCTCATCTGAAAAAACTTGTGAAAATACGT   185

AATCCTGATGAGACTTCAATTAGGTATAAAAACCAGCCCCAGAAGGCGAGGCAGTACACT   245

CTTCTGATCGCCGGTAGGGCAGCTATTAGAAAAGAAAGATCAGCTGAGGCCTTGGGACCT   305

GATCAGCTTAGTACAGAAGTGACTGCTTTCAACTACTTAGGCCTAACTCTCTCCGAAACA   365

-20                 -15                 -10
Met Asn Tyr Thr Ser Phe Ile Leu Ala Phe Gln Leu Cys Ala Ile
ATG AAT TAT ACA AGT TTT ATC TTG GCT TTT CAG CTG TGT GCG ATT    410
```

-continued

```
 -5                   -1    1               5                        10
Leu  Gly  Ser  Ser  Thr  Tyr  Tyr  Cys  Gln  Ala  Ala  Phe  Phe  Lys  Glu
TTG  GGT  TCT  TCT  ACC  TAT  TAC  TGC  CAG  GCC  GCG  TTT  TTT  AAA  GAA        455

                    15
Ile  Glu  Asn  Leu  Lys  Glu  Tyr  Phe
ATA  GAA  AAC  CTA  AAG  GAA  TAT  TTT  GTAAGTATGACCTTTTAATAATACTTAC        507
     INTRON 1

TTGTGGTTGAAATGACTGAACGTTGTCTTGGAGTTGGATCTCTGATAGGCTGTCCTCTCT        567

ACTCCACAGTCATCTTGAGAAGACTGGGTGTTATTTTCTCTGTTTGTTGACTGGATGAGT        6277

TTTTCTTTTTTTTACTAAATGATCTAGATATTGCTTTAACCCTCTGCTCAATTTGCTATA        687

GAGACTTAGAGAGGGTTCATGAATCTTCCAAAAGATGGGCTTAACAGGTTTATAAAGCAT        747

AGTGAAGTTGACAATTTTGTGGTGAGAAGCCACTGAATTGTGATAAGTCAAGTAGTGTGG        807

ACATTGAAAAAATGACTAGCTATTAGTTTCTAACTTCTCAGGTTACTATGATGGTGACAA        867

TAAAAGGTCAAGATTAGCATTAAAATGGTAATCTGAAATAATTGATCAGTTAAAGAAGGC        927

GCTGTCCTGAAAGGTTTGGCTGAAAAAAAATCACTTTCAGGTGTTTTCCTCCAAAAAATG        987

ATTTTAAAATCTTACTGCCCCGTTTGTGTTAGCTGTGAAGTACTCTGGAACTCAGTCAAT        1047

TGCTGAGATTTTGTACGAGTTATAAGCTGGCTTATATTTAAAAAATTTTTTTGTTTTTGT        1107

TTTATGAGTTTCTTTTAAAATGTTATTTATGGTTAATTAAAATAGTTTTTGCATTTTAAA        1167

TATTTTATTATTTGTCCAAAATTTAGCTATTTTAATTATAGTTGGAGCTCTCTTTTAGAG        1227

CTGACATAAGACCATAGGGGAGGCACAGATAGATGTGATGGAGCCCTGTACCAGACGGGG        1287

GCAGTATCTTATAGTGGGTTGCCTTTGCTGATCTTTTTACTAGACTTGAAATTATTTGCT        1347

TTTCCTTCCTATGGTTATTTGGGACTATTGAAGTATCACCAGCCCTGTTGAGTTCATCTG        1407

TAATATTGTAATTCAAGGGTTACACTAGAAAATAAGAAAGCTAAAACAGCACGATAATCT        1467

TTGGCTACATCCAACACAATAGCTTTTGGGAATACTTATTGTTAGAACTAAACAGAGGGT        1527

TGAAAAGAAAATCAGTGAATACTGTCAGCATCTGAGTTCAATAAAACGTGAAGTACATTT        1587

                                                            20
                                                       Asn  Ala
TTAGGGCAATTCATGGACTAATTGTAAACCAAGTTTTCCTTCCTTTTTCAG  AAC  GCA        1644

                    25                  30                  35
Arg  Asn  Pro  Asp  Val  Gly  Asp  Gly  Gly  Pro  Leu  Phe  Leu  Asp  Ile
AGA  AAC  CCA  GAT  GTA  GGG  GAT  GGT  GGG  CCT  CTT  TTC  CTG  GAT  ATC        1689

                    40                       INTRON 2
Leu  Lys  Asn  Trp  Lys  Glu
TTG  AAG  AAC  TGG  AAA  GAG  GTAAGCTAAGTATTTCCATTTGGTTGATTTTCCTGT        1743

TGCTTATTTTCTGGTGGATGAATTCACACCAACCTCTCTTTGTGCTCTTTTCTCCCTAG        1802

               45                  50                  55
Asp  Ser  Asp  Lys  Lys  Ile  Ile  Gln  Ser  Gln  Ile  Val  Ser  Phe  Tyr
GAT  AGT  GAC  AAA  AAA  ATA  ATT  CAG  AGC  CAA  ATC  GTC  TCC  TTC  TAC        1847
```

-continued

```
                    60                          65                          70
Phe  Lys  Leu  Phe  Glu  Asn  Leu  Lys  Asp  Asn  Gln  Val  Ile  Gln  Lys
TTC  AAA  CTC  TTT  GAA  AAC  TTG  AAA  GAT  AAC  CAG  GTC  ATT  CAA  AAG      1892

                    75                          80                          85
Ser  Met  Asp  Thr  Ile  Lys  Glu  Asp  Leu  Phe  Val  Lys  Phe  Phe  Asn
AGC  ATG  GAC  ACC  ATC  AAG  GAG  GAC  CTG  TTC  GTT  AAG  TTC  TTT  AAC      1937

                    90                          95                          100
Ser  Ser  Thr  Ser  Lys  Leu  Glu  Asp  Phe  Gln  Lys  Leu  Ile  Gln  Ile
AGC  AGC  ACC  AGC  AAG  CTG  GAA  GAC  TTC  CAA  AAG  CTG  ATT  CAG  ATT      1982

               INTRON
Pro
CCG GTGAGGAGATCTTAATTCTTTCTTTGGTTTCATTACAGAGGTTCTTGCAAAGTGCT     2041

TACGTCCCAGAAAGTAGAAATGAACTATGAAATGAACCCGTGGCCAAAACTCCTCCTTCC     2101

TAATTCCATTTGTGCTTTGAGAGACTTTGCTAAGTCAGTATGGGAATCATTTAAATTGT      2161

GATTTGGGGAAATGCTGGCACTATGACTACTGCACAAAGGCAGGTGAAGGGACAAATCCA     2221

GTGAGGAGGGGGCAGTGAAGAAGTGGAGGGGAGTCTGGAGAAGCAGGTCTCTCCTTGCCC     2281

CTTGTTCGTGAGATGAAATCCTCCTGCTTTGGATGGGAGGCTGCGTGTCTTGGTGGAAAG     2341

AGCAGTGGGAGGAGGGAGAAGATTTGTGCTCCTCCCAGCTCAGCCACCAAGAAACTGTGA     2401

CCTCAGATGAATCACAGGCCTGGCTGGGGCTCAGTTTCCTCATCTTAAAAGAGGCCTATT     2461

GGGTTCACTAAAATTTCTATGATCTTCTTTGCTCTATAATCCTACAATTCTGTGGACAGA     2521

AAATGAAATGAGGTAGGAGAAAGAAATAGCCTTTGAAGAGGTTCTTGGGCATTCCACTGC     2581

CAGGCTCTGGTCAACCTTCATACTCTGCAGCCCAAGAAGAGGCAAGACCATTTGTCTGTT     2641

TTTGGAAATGCAAATAGGCGGCATTTATACCTCACGAAAGAACTGTTCTGTCAACTTTTG     2701

GATACTGGGCTATCTTGGCTGGAGAAATCCTTAGGCTCCCAAACTTTCTCTCATGAAATT     2761

GTCTTGAGTCTTTAAATTTATGGCTTCTCGAAGCTGAGAGATAACTTTAAGCATAAAGAC     2821

AAATTACATTTTCCAACATTTTGTCTAAGAGACAAAGACCTCCACATGCCTTTGGGTTTG     2881

GCCTGGATCTAAATGGGCTTGAATGAGAAGGGGAGGGTGTTGTTATGACTATGTTTAGAA     2941

GAGAAAACAGAGGTTTGGAGAGGTTAAGTGGCTGGTTCAAAGTCAGAGTTATTGCACACA     3001

CAGGATTCGAACCCATATGTTTTGTCCCTCCACTTTAGGGTTCTTTTCGCTACATAATTT     3061

TGAGAATTCTGTACCAGTCAATTTAAGGATGTGTGATGTTCCCCATCCTATTACAGCACA     3121

ACCAGCAATTTAATTATAATTTTAGTCTTAACTGCTGAAGAAAGCAGCATTACATATTAA     3181

GCTAACATATTCCTGGTGAAAGCAACTTTTTCAAAGGAATATTTCTATTTTCATGGACCA     3241

TGACAGTAGCACAGCCTGATGGCTTGTATGCCTGAAACTAATTTTGCTGTTTTCTTTCCC     3301

                      105                          110                          115
        Val  Asn  Asp  Leu  Lys  Val  Gln  Arg  Lys  Ala  Ile  Ser  Glu  Leu
AATAG   GTA  AAT  GAT  CTG  AAG  GTC  CAG  CGC  AAA  GCA  ATA  AGT  GAA  CTC      3348
```

-continued

| | | | | | | | | | | | | | | | |
|---|---|---|---|---|---|---|---|---|---|---|---|---|---|---|---|
| | | | 120 | | | | | 125 | | | | | 130 | | |
| Ile | Lys | Val | Met | Asn | Asp | Leu | Ser | Pro | Lys | Ala | Asn | Leu | Arg | Lys | |
| ATC | AAA | GTG | ATG | AAT | GAT | CTG | TCG | CCC | AAA | GCT | AAC | CTG | AGG | AAG | 3393 |
| | | | 135 | | | | | 140 | | | | | 145 | | |
| Arg | Lys | Arg | Ser | Gln | Asn | Pro | Phe | Arg | Gly | Arg | Arg | Ala | Leu | Gln | |
| CGG | AAG | AGG | AGT | CAG | AAT | CCA | TTT | CGA | GGC | CGG | AGA | GCG | TTG | CAA | 3438 |

```
***
TAG TGGTCATCCTGCCTGCAATATTTGAATTTTTAATCTAAATCTATTTATTAATATT   3497
TAATATTTTACATTATTTATATGGGGAATATATTTTTAAACTCATCAAAGTATTTATAAT  3557
AGCAACTTTTATGTAATGAAAATGGGTATCTATTAATATATATATTATTTATAATTCCTG  3617
TATGGTGTGACTATTTCACTTGACCCTTTTTTTTCTGACCAACTAGGCAAGATTATGTGA  3677
TTACAAGGCTTTAACTCAGGGGCCAACTAGGGAGTGGGTAGCCGACCTACCAAGACCCTG  3737
TGAGCTGTGTGTTTATTTCCCTCAATGATACAATGAACACTTATAAAGGAAAGGAGGGCC  3797
TCCAGTCACTGCCTGTTGGAGAACATGTCTGCATTGTGAGCCACTGCTTAATGGCATGTC  3857
AAACCACGCTTGAATGTGTCAGATGATAGGGCTTGTCCCCTGATAAAGCTTAGTATCTCC  3917
TCTCATGCCTAGTGCTTCAGAATATTGTTGACAACTGTGACTGCACCCAAATGGAAAGTA  3977
ATTTATTTGTTTAGTTTACCAATATTTAATAAATATGAATAAAGTATAATTTCATAACTA  4037
TTTATGCTGCGTCCGGCTTTTTCTAAGTGAGGACTGGGGTAAATGAACTACAAACTAATG  4097
AATCAGTAAGAGGGAACTCGTTTTTAGCGGTGGAAATCTTAGCTGGATTAAGCCCCATGA  4157
AACGTGGTATTTCTCTCCACTGGAGATTTGTTGGCTACTACTCCTCCATGTAGCAGCTCT  4217
TTATCTTTCCAAAATATAAATTTAATTATGTCACCATTTACTTCAGAGCTTCTGCGATGG  4277
AAAGTAGTTCAAATAGTTTAGCTTAGCACACAAAGCTTTGTTTCTCCCTCCTCCCTCAAC  4337
TCTGCACTGTGCTCTTCATCTTGGTGTCCCCACGTCCTCTGTCCACTTCGGGCAAACCAC  4397
CGGGAATGTCATGGTGAGGGTGAGCTCTAGGGAGAGAGGGCTGGATTAGAATTTCGGCCC  4457
CACCATTACCAGTAGTATGACCTTTAATGAATTACTTGTATTCTCTAAGCTCCAGTTTCC  4517
TCATCTGACACAAGAGAATAATTGTGCCTAAAATTGTGGTGAGAGTTTGTTCTTTCACTC  4577
AAGAAGTGTTTACTGGAGCATCCACTAGTTGCCTAGTGCTGTTCTAGGCACTTGAGATAC
ATTTGTGAACAAAATAGTCAAGGATCC                                   4664
```

It is noticeable that EqIFN-γ, like all the γ-interferons which have been known hitherto, is encoded in the organism in question by a gene which has long sequences which interrupt the structural gene: the genes consist of exons and introns, with only the exons coding for the protein. The introns can only be understood by certain systems, for example systems in mammalian cells. DNA sequences which contain introns cannot be used for other systems, for example in *E. coli.*

A further aim of this invention was therefore to prepare an intron-free DNA sequence coding for EqIFN-γ.

This aim can be achieved, in principle, in two ways.

1. From the cell nucleus, in which transcription takes place, the introns are excised in the cytoplasm and, by splicing the exon-RNA fragments, the mRNA of the eukaroytic protein is produced. This mRNA can be recopied with an enzyme, namely reverse transcriptase, into a DNA which is referred to as copy-DNA (cDNA).

Formula II

```
  1               5                  10                 15
TAT TAC TGC CAG GCC GCG TTT TTT AAA GAA ATA GAA AAC CTA AAG

                 20                  25                 30
GAA TAT TTT AAC GCA AGA AAC CCA GAT GTA GGG GAT GGT GGG CCT

                 35                  40                 45
CTT TTC CTG GAT ATC TTG AAG AAC TGG AAA GAG GAT AGT GAC AAA

                 50                  55                 60
AAA ATA ATT CAG AGC CAA ATC GTC TCC TTC TAC TTC AAA CTC TTT

                 65                  70                 75
GAA AAC TTG AAA GAT AAC CAG GTC ATT CAA AAG AGC ATG GAC ACC

                 80                  85                 90
ATC AAG GAG GAC CTG TTC GTT AAG TTC TTT AAC AGC AGC ACC AGC

                 95                 100                105
AAG CTG GAA GAC TTC CAA AAG CTG ATT CAG ATT CCG GTA AAT GAT

                110                 115                120
CTG AAG GTC CAG CGC AAA GCA ATA AGT GAA CTC ATC AAA GTG ATG

                125                 130                135
AAT GAT CTG TCG CCC AAA GCT AAC CTG AGG AAG CGG AAG AGG AGT

                140                 145
CAG AAT CCA TTT CGA GGC CGG AGA GCG TTG CAA TAG
```

This intron-free DNA can then be inserted into suitable plasmids which may then be used together with suitable host organisms, for example *E. coli*, for producing eukaryotic proteins, in this instance from EqIFN-γ. One disadvantage of this method is the degeneracy of the genetic code. In fact, this degeneracy causes different organisms to use different codons for the same amino acids. Therefore, if the DNA used is not optimally suited, this may result in impaired expression of a eukaryotic protein in a prokaryotic system.

2. The other possible way of obtaining an intron-free DNA sequence for a eukaryotic gene is to synthesise an intron-free DNA sequence chemically, provided that the chromosomal DNA sequence is known.

The DNA sequence according to Formula III has proved particularly suitable for solving the problem of the invention:

This can be prepared by methods known per se. 16 different oligonucleotides were synthesised in two variants. The first complete variant codes for mature EqIFN-γ with 146 amino acids plus start-methionine (Formula III), whilst the second codes for a polypeptide shortened by 3 amino acids at the amino terminus, plus start-methionine.

Formula III

```
 -1   1               5                  10                 15
ATG TAC TAC TGC CAG GCT GCT TTC TTT AAA GAA ATC GAA AAC CTG AAA

                 20                  25                 30
GAA TAC TTC AAC GCT CGT AAC CCA GAC GTT GGT GAC GGT GGT CCG

                 35                  40                 45
CTG TTC CTG GAC ATC CTG AAA AAC TGG AAA GAA GAC TCT GAC AAA

                 50                  55                 60
AAG ATC ATC CAG TCT CAG ATC GTT TCT TTC TAC TTC AAA CTG TTC

                 65                  70                 75
GAA AAC CTG AAA GAC AAC CAG GTT ATC CAG AAA TCG ATG GAC ACT

                 80                  85                 90
ATC AAA GAA GAT CTG TTC GTT AAA TTC TTC AAC TCG TCG ACT TCT

                 95                 100                105
AAA CTG GAA GAC TTC CAG AAA CTG ATC CAG ATC CCA GTT AAC GAC

                110                 115                120
CTG AAA GTT CAG CGT AAG GCT ATC TCT GAA CTG ATC AAA GTT ATG

                125                 130                135
AAC GAC CTG TCT CCA AAA GCT AAC CTG CGT AAA CGT AAA CGT TCT

                140                 145
CAG AAC CCA TTC CGT GGT CGT CGT GCT CTT CAG TAA
```

```
 -1   1                5                    10                        15        Formula IIIa
ATG CAG GCT GCT TTC TTT AAA GAA ATC GAA AAC CTG AAA GAA TAC TTC

               20                    25                    30
AAC GCT CGT AAC CCA GAC GTT GGT GAC GGT GGT CCG CTG TTC CTG

               35                    40                    45
GAC ATC CTG AAA AAC TGG AAA GAA GAC TCT GAC AAA AAG ATC ATC

               50                    55                    60
CAG TCT CAG ATC GTT TCT TTC TAC TTC AAA CTG TTC GAA AAC CTG

               65                    70                    75
AAA GAC AAC CAG GTT ATC CAG AAA TCG ATG GAC ACT ATC AAA GAA

               80                    85                    90
GAT CTG TTC GTT AAA TTC TTC AAC TCG TCG ACT TCT AAA CTG GAA

               95                   100                   105
GAC TTC CAG AAA CTG ATC CAG ATC CCA GTT AAC GAC CTG AAA GTT

              110                   115                   120
CAG CGT AAG GCT ATC TCT GAA CTG ATC AAA GTT ATG AAC GAC CTG

              125                   130                   135
TCT CCA AAA GCT AAC CTG CGT AAA CGT AAA CGT TCT CAG AAC CCA

              140        143
TTC CGT GGT CGT CGT GCT CTT CAG TAA
```

Both variants can easily be modified by adding on a sequence coding for a hydrophobic signal peptide, for example a sequence of formula IV, instead of the ATG coding for methionine.

```
ATG AAT TAT ACA AGT TTT ATC TTG GCT TTT CAG CTG TGT GCG ATT                Formula V
TTG GGT TCT TCT ACC
```

A signal sequence of this kind will, in certain host organisms, bring about secretion of the desired polypeptide from the cytoplasm. Thence the protein is processed and the signal peptide is cleaved; the mature protein is obtained. Cells from host organisms, for example *E. coli*, which are not capable of processing polypeptides containing the signal peptide sequence must be broken up in order to isolate the "immature" polypeptide. These "immature" EqIFN-γ's with complete or incomplete signal peptide sequences are also an object of this invention.

The start-methionine may be separated by known methods, e.g. using CNBr or CNCl, in order to obtain mature EqIFN-γ.

This DNA sequence codes for EqIFN-γ but contains exclusively those codons, highly expressed by *E. coli*, which are used in genes native to the cell (Gouy and Gautier, Nucl. Acids Res. 10, 7055 (1982)).

A further object of the invention was to prepare EqIFN-γ in a pure, homogeneous form for the first time.

As already mentioned, isolation and purification of EqIFN-γ from natural cell material is not capable of solving this problem in a satisfactory manner. According to the invention, therefore, the DNA sequences according to formulae II, III and IIIa are used to solve this problem. These sequences, provided with corresponding control sequences, are incorporated into suitable vectors and suitable host organisms or host cell cultures transformed therewith are cultivated. The polypeptides formed are isolated and purified by methods known per se.

The polypeptides obtained correspond to the following formula:

```
 1                    5                        10                      15         Formula V
Tyr Tyr Cys Gln Ala  Ala Phe Phe Lys  Glu Ile Glu Asn Leu  Lys

                     20                        25                      30
Glu Tyr Phe Asn Ala  Arg Asn Pro Asp  Val Gly Asp Gly Gly  Pro

                     35                        40                      45
Leu Phe Leu Asp Ile  Leu Lys Asn Trp  Lys Glu Asp Ser Asp  Lys

                     50                        55                      60
Lys Ile Ile Gln Ser  Gln Ile Val Ser  Phe Tyr Phe Lys Leu  Phe

                     65                        70                      75
Glu Asn Leu Lys Asp  Asn *Gln Val Ile  Gln Lys Ser Met Asp  Thr

                     80                        85                      90
Ile Lys Glu Asp Leu  Phe Val Lys Phe  Phe Asn Ser Ser Thr  Ser

                     95                       100                     105
Lys Leu Glu Asp Phe  Gln Lys Leu Ile  Gln Ile Pro Val Asn  Asp
```

-continued

| | | | | | | | | | | | | | | |
|---|---|---|---|---|---|---|---|---|---|---|---|---|---|---|
| | | | | 125 | | | | | 130 | | | | | 135 |
| Asn | Asp | Leu | Ser | Pro | Lys | Ala | Asn | Leu | Arg | Lys | Arg | Lys | Arg | Ser |
| | | | | 140 | | | | | 145 | | | | | |
| Gln | Asn | Pro | Phe | Arg | Gly | Arg | Arg | Ala | Leu | Gln *** | | | | |

or

Formula Va

| | | | | | | | | | | | | | | |
|---|---|---|---|---|---|---|---|---|---|---|---|---|---|---|
| | | | Gln | Ala | Ala | Phe | Phe | Lys | Glu | Ile | Glu | Asn | Leu | Lys |
| Glu | Tyr | Phe | Asn | Ala | Arg | Asn | Pro | Asp | Val | Gly | Asp | Gly | Gly | Pro |
| Leu | Phe | Leu | Asp | Ile | Leu | Lys | Asn | Trp | Lys | Glu | Asp | Ser | Asp | Lys |
| Lys | Ile | Ile | Gln | Ser | Gln | Ile | Val | Ser | Phe | Tyr | Phe | Lys | Leu | Phe |
| Glu | Asn | Leu | Lys | Asp | Asn | Gln | Val | Ile | Gln | Lys | Ser | Met | Asp | Thr |
| Ile | Lys | Glu | Asp | Leu | Phe | Val | Lys | Phe | Phe | Asn | Ser | Ser | Thr | Ser |
| Lys | Leu | Glu | Asp | Phe | Gln | Lys | Leu | Ile | Gln | Ile | Pro | Val | Asn | Asp |
| Leu | Lys | Val | Gln | Arg | Lys | Ala | Ile | Ser | Glu | Leu | Ile | Lys | Val | Met |
| Asn | Asp | Leu | Ser | Pro | Lys | Ala | Asn | Leu | Arg | Lys | Arg | Lys | Arg | Ser |
| Gln | Asn | Pro | Phe | Arg | Gly | Arg | Arg | Ala | Leu | Gln *** | | | | |

When the chromosomal sequence (formula II) is used, after transformation of mammalian cells, EqIFN-γ is obtained in its naturally occurring, glycosylated form (authentic EqIFN-γ). The sequences according to formulae II, III and IIIa are particularly suitable for the preparation of EqIFN-γ in microorganisms, particularly for the preparation of EqIFN-γ in *E. coli*, the polypeptide being expressed in non-glycosylated form.

A further object of this invention is to prepare modifications of the natural EqIFN-γ.

Modifications of a protein may be obtained either by derivatising the protein or by fragmenting it by enzyme digestion or by modifying the DNA sequence which encodes the protein by deletion or fragmentation and expressing this sequence in a suitable host organism.

According to the invention, the DNA sequences coding for modifications of EqIFN-γ are synthesised chemically. To permit simple manipulation of the gene in order to change individual sections, a plurality of single restriction enzyme cutting sites are incorporated in the complete DNA sequence.

Other modified forms of EqIFN-γ are obtained according to the invention by incorporating the various oligonucleotides in suitable vectors, either alone or in various combinations, equipped with the corresponding control sequences, cultivating the host organisms transformed therewith and isolating and purifying the resulting proteins.

In order to achieve these objectives, high molecular weight DNA was isolated from horse tissue, preferably the liver, using a modified method according to Blin and Stafford (Blin, N., Stafford, P. W.; Nucl. Acids Res. (1976), 3, 2303–2308) and statistically fragmented using special endonucleases. The fragments of different sizes thus obtained were fractionated according to their size, preferably to form fragments of 10–23 kb, for cloning in a vector, for example a lambda vector, e.g. lambda EMBL3A. These vectors were then replicated after transformation into a host organism, for example *E. coli*. This equine DNA library was searched by means of a human gamma-interferon probe under non-stringent hybridisation conditions. The low level of stringency makes it possible to find DNA sequences which differ from the probe.

It may be prepared either by digesting plasmids known from the literature by means of restriction enzymes or by chemical synthesis using known methods of synthesising oligonucleotides. This probe has the sequence coding for HuIFN-γ. Five lambda clones were identified, which yielded positive hybridisation signals.

The DNA was purified from these isolated recombinant phages by conventional methods. The phage DNA's were characterised, after digestion with various restriction enzymes and subsequent Southern analysis (Southern, J. Mol. Biol. 98: 503–517, 1975) by hybridisation with the HuIFN-γ probe. A single hybridising BamHI fragment, 4.6 kb long, of the clone lambda Eq-γ2 was isolated and cloned into the BamHI cutting site of the plasmid pUC9 (Vieira and Messing, Gene 19: 259–268, 1982).

After transformation of *E. coli*, for example JM101, plasmid DNA was prepared from the resulting colonies by a mini-preparation method (Birnboim and Doly, Nucl. Acids Res. 7: 1513–1523, 1979) and characterised by digestion with restriction enzymes. A plasmid having the desired BamHI insert was designated pAH111. After introduction into the M13mp8 or M13mp9 vectors (Vieira and Messing, Gene 19, 259–268, 1982), the ends of the BamHI insert of plasmid pAH111 were sequenced by the dideoxy method (Sanger et. al., Proc. Natl. Acad. Sci. USA 74: 5463–5467, 1977). A sequence comparison with the human gamma-interferon gene (Gray and Goeddel, Nature 298: 859–863, 1982) showed a high degree of homology with the non-coding 5'- and 3'- regions. It was therefore concluded that the complete EqIFN-γ gene had been isolated.

The 4.6 kb long BamHI insert of plasmid pAH111 was totally sequenced by the dideoxy method. The total sequence of the BamHI fragment was determined by combining partial sequences from M13 subclones, which had been obtained by directed cloning of restriction fragments (EcoRI, HindIII, PstI, PstI-BglII, HindIII-BamHI) into correspondingly cut M13mp8 or M13mp9 vectors. Other partial sequences were obtained by cloning the 2.0 kb long BamHI-BglII fragment or the 2.0 kb long PstI fragment into the M13mp8 vector by the "Shotgun" method. The partial sequences obtained were combined by means of a computer program to give the total sequence 4664 bp long which is shown in FIGS. 1A–1C.

By computer-aided analysis of the open reading frame and comparison with gamma-interferon genes of other species (Gray and Goeddel, Nature 298: 859–863; Gray and Goeddel, Proc. Natl. Acad. Sci. USA 80: 5842–5846, 1983; Dijkema et al., EMBO J. 4: 761–767, 1985; Cerretti et al., J. Immunology 136: 4561–4564, 1986) the protein-coding region of the equine gamma-interferon gene was determined. The protein-coding region is interrupted by three introns, the first exon encoding the hydrophobic signal peptide which is 20 amino acids long and 18 amino acids of the mature EqIFN-γ polypeptide (bases 366–479). The second exon codes for amino acids 19–41 (bases 1639–1707), the third exon codes for amino acids 42–102 (bases 1803–1985), the fourth exon encodes the carboxy terminus with amino acids 103–146 (bases 3307–3441). At positions 4010 and 4020 there are two signal sequences (AATAAA) for the polyadenylation of mRNA. At positions 86–88 of the mature EqIFN-γ polypeptide is the single potential N-glycosylation site (ASN-Ser-Ser), which coincides with the second N-glycosylation site of bovine gamma-interferon (Asn-Gly-Ser) (FIG. 2). Surprisingly, the mature EqIFN-γ polypeptide contains only one single cysteine group at position 3, whilst analogously to natural human and murine gamma-interferons the first three amino-terminal amino acids (in this case Tyr-Tyr-Cys) are probably cleaved proteolytically in the body.

In order to express recombinant EqIFN-γ in its mature form in *Escherichia coli*, a synthetic gene was constructed from oligonucleotides. It codes for the same amino acid sequence as the natural EqIFN-γ gene, but contains only those codons for the individual amino acids which are used in native cell genes highly expressed by *E. coli* (Gouy and Gautier, Nucl. Acids Res. 10: 7055–7074, 1982). In addition, several single restriction enzyme cutting sites were incorporated, permitting easy manipulation of the gene in order to change individual sections. The synthetic gene for EqIFN-γ was constructed in two alternative forms from a total of 16 different oligonucleotides. The first variant codes for mature EqIFN-γ with 146 amino acids plus start-methionine, whilst the second form codes for a polypeptide shortened by 3 amino acids (Tyr-Tyr-Cys) at the amino terminus, plus start-methionine, as would presumably occur in the natural organism.

The structure of the synthetic EqIFN-γ gene is illustrated in FIGS. 3A and 3B. The oligonucleotides used for its preparation were synthesised using an Applied Biosystems Model 381A DNA synthesiser, purified by electrophoresis and desalinated. The oligonucleotides characterised in FIGS. 3A and 3B have the following structure:

| | | | | | | |
|---|---|---|---|---|---|---|
| EG-1 | 5'- TACTACTGCC CTTCAACGCT | AGGCTGCTTT CG-3' | CTTTAAAGAA | ATCGAAAACC | TGAAGAATA | |
| EG-2 | 5'- TTGAAGTATT GTAGTA-3' | CTTTCAGGTT | TTCGATTTCT | TTAAAGAAAG | CAGCCTGGCA | |
| EG-3 | 5'- TAACCCAGAC ACTGGAAAGA | GTTGGTGACG AGACTCTG-3' | GTGGTCCGCT | GTTCCTGGAC | ATCCTGAAAA | |
| EG-4 | 5'- TTCTTTCCAG CGTCTGGGTT | TTTTTCAGGA ACGAGCG-3' | TGTCCAGGAA | CAGCGGACCA | CCGTCACCAA | |
| EG-5 | 5'- ACAAAAAGAT GAAAACCTGA | CATCCAGTCT AAGACAACC-3' | CAGATCGTTT | CTTTCTACTT | CAAACTGTTC | |
| EG-6 | 5'- TTTCAGGTTT TGATCTTTTT | TCGAACAGTT GTCAGAGTC-3' | TGAAGTAGAA | AGAAACGATC | TGAGACTGGA | |
| EG-7 | 5'- AGGTTATCCA TTCTTCAACT | GAAATCGATG CG-3' | GACACTATCA | AAGAAGATCT | GTTCGTTAAA | |
| EG-8 | 5'- TCGACGAGTT GATTTCTGGA | GAAGAATTTA TAACCTGGTT | ACGAACAGAT GTC-3' | CTTCTTTGAT | AGTGTCCATC | |
| EG-9 | 5'- TCGACTTCTA CGACCTGAAA-3' | AACTGGAAGA | CTTCCAGAAA | CTGATCCAGA | TCCCAGTTAA | |
| EG-10 | 5'- GCTGAACTTT TCCAGTTTAG | CAGGTCGTTA AAG-3' | ACTGGGATCT | GGATCAGTTT | CTGGAAGTCT | |
| EG-11 | 5'- GTTCAGCGTA TCCAAAAGCT | AGGCTATCTC AA-3' | TGAACTGATC | AAAGTTATGA | ACGACCTGTC | |
| EG-12 | 5'- CGCAGGTTAG GATAGCCTTA | CTTTTGGAGA C-3' | CAGGTCGTTC | ATAACTTTGA | TCAGTTCAGA | |
| EG-13 | 5'- CCTGCGTAAA TTCAGTAAG-3' | CGTAAACGTT | CTCAGAACCC | ATTCCGTGGT | CGTCGTGCTC | |
| EG-14 | 5'- GATCCTTACT ACGTTTA-3' | GAAGAGCACG | ACGACCACGG | AATGGGTTCT | GAGAACGTTT | |
| EG-15 | 5'- CAGGCTGCTT | TCTTTAAAGA | AATCGAAAAC | CTGAAAGAAT | ACTTCAACGC | TCG-3' |
| EG-16 | 5'- TTGAAGTATT | CTTTCAGGTT | TTCGATTTCT | TTAAAGAAAG | CAGCCTG-3' | |

The synthetic EqIFN-γ gene was put together in two sections. The first part of the gene, up to the SalI cutting site, was produced using the eight oligonucleotides EG-1 to EG-8 whilst the second half of the gene, from the SalI cutting site to the BamHI cutting site, was prepared from the six oligonucleotides EG-9 to EG-14. For the form of EqIFN-γ shortened by three amino acids at the amino terminus, the oligonucleotides EG-15 and EG-16 were used instead of the oligonucleotides EG-1 and EG-2.

The invention relates not only to genetic sequences which code specifically for the interferons according to the invention but also to modifications which can easily and routinely be obtained by mutation, degradation, transposition or addition. Any sequence which codes for the interferons according to the invention (i.e. which has the biological spectrum of activity described herein) and is degenerate compared with those shown, is also included; anyone skilled in the art is capable of degenerating DNA sequences of the coding regions. Similarly, any sequence which codes for a polypeptide with the spectrum of activity of the interferons according to the invention and which hybridises with the sequences shown (or parts thereof) under stringent conditions (e.g. conditions which select for more than 85%, preferably more than 90% homology) is also included.

The hybridizations are carried out in 6×SSC/5×Denhardt's solution/0.1% SDS at 65° C. The degree of stringency is determined in the washing step. Thus, for selection of DNA sequences with approximately 85% or more homology, suitable conditions are 0.2×SSC/0.01% SDS/65° C. and for selection of DNA sequences with approximately 90% homology or more, the suitable conditions are 0.1×SSC/0.01% SDS/65° C.

Interferon genes according to the invention may be introduced into any organism under conditions which result in high yields. Suitable hosts and vectors are best known to those skilled in the art; by way of example, reference is made to EP-A-0093619.

Prokaryotes are particularly preferred for expression, for example *E. coli* K 12, strain 294 (ATCC No. 31 446) or *E. coli* X 1776 (ATCC No. 31537). Apart from the above mentioned strains it is also possible to use *E. coli* W 3110 ($F^-$, lambda$^-$, prototroph, ATCC No. 27325), Bacilli such as *Bacillus subtilis* and other Enterobacteriaceae, such as *Salmonella typhimurium* or *Serratia marcescens* and various Pseudomonads.

In general, plasmid vectors which contain control sequences originating from species which are compatible with the host cells may be used in conjunction with these hosts. The vector usually carries, in addition to a replication site, recognition sequences which make it possible to phenotypically select the transformed cells. For example, *E. coli* is usually transformed with pBR322, a plasmid which originates from the species *E. coli* (Bolivar, et al., Gene 2, 95 (1977)). pBR322 contains genes coding for ampicillin and tetracycline resistance and thus affords a simple means of identifying transformed cells. The pBR322 plasmid or other plasmids must, in addition, contain promoters themselves or must be modified so that they contain promoters which can be used by the microbial organism for the expression of its own proteins. The promoters most frequently used in the preparation of recombinant DNA include the beta-lactamase (penicillinase) and lactose promoter systems (Chang et al., Nature 275, 615 (1978); Itakura et al., Science 198, 1056 (1977); Goeddel et al., Nature 281, 544 (1979)) and tryptophan(trp) promoter systems (Goeddel et. al., Nucleic Acids Res. 8, 4057 (1980); EP-A-0036776). Whereas these are the most commonly used promoters, other microbial promoters have also been developed and used. The genetic sequence for the interferons according to the invention may be used, for example, under the control of the leftward promoter of the bacteriophage lambda ($P_L$). This promoter is one of the promoters known to be particularly powerful and is also controllable. Control is made possible by the lambda repressor of which adjacent restriction cutting sites are known. A temperature-sensitive allele of this repressor gene may be inserted into a vector which contains an EqIFN-γ sequence. If the temperature is increased to 42° C., the repressor is inactivated and the promoter is activated.

By using this system it is possible to establish a clone bank in which a functional IFN sequence is placed close to a ribosome binding site at varying distances from the lambda $P_L$ promoter. These clones can then be checked and those with the highest yield selected.

The expression and translation of a sequence coding for the proteins according to the invention may also be effected under the control of other regulating systems which may be regarded as "homologous" to the organism in its untransformed form. Thus, for example, chromosomal DNA from a lactose-dependent *E. coli* contains a lactose or lac-operon which allows the degradation of lactose by secreting the enzyme beta-galactosidase. The lac-control elements may be obtained from the bacteriophage lambda-plac5, which is infectious for *E. coli*. The lac-operon of the phage may be obtained from the same bacterial species by transduction.

Regulating systems which may be used in the process according to the invention may originate from plasmid DNA which is native to the organism. The lac-promoter, operator system may be induced by IPTG.

Other promoter-operator systems or parts thereof may be used with equally good effect: for example, arabinose operator, colicin $E_1$-operator, galactose operator, alkaline phosphatase operator, trp operator, xylose-A operator, tac-promoter, etc.

In addition to prokaryotes, eukaryotic microorganisms such as yeast cultures may also be used. *Saccharomyces cerevisiae* is the most commonly used of the eukaryotic microorganisms, although a number of other species are generally obtainable. For expression in *Saccharomyces*, for example the plasmid YRp7 (Stinchcomb et al., Nature 282, 39 (1979); Kingsman et al., Gene 7, 141 (1979); Tschumper et al., Gene 10, 157 (1980)) and the plasmid YEp13 (Bwach et al., Gene 8, 121–133 (1979)) are conventionally used. The plasmid YRp7 contains the TRP1 gene which is a selectable marker in a yeast mutant which is incapable of growing in tryptophan-free medium; for example ATCC No. 44076.

The presence of the TRP1 defect as a characteristic of the yeast host genome constitutes an effective aid to detecting transformation, in which cultivation is carried out without tryptophan. The situation is very similar with the plasmid YEp13, which contains the yeast gene LEU 2, which can be used to complement a LEU-2-minus mutant. Suitable promoter sequences for yeast vectors contain the 5'-flanking region of ADH I (Ammerer G., Methods of Enzymology 101, 192–201 (1983)), 3-phosphoglycerate-kinase (Hitzeman et al., J. Biol. Chem. 255, 2073 (1980)), or other glycolytic enzymes (Kawasaki and Fraenkel, BBRC 108, 1107–1112 (1982)) such as enolase, glyceraldehyde-3-phosphate dehydrogenase, hexokinase, pyruvate decarboxylase, phosphofructokinase, glucose-6-phosphate isomerase, phosphoglucose isomerase and glucokinase. By constructing suitable expression plasmids the termination sequences associated with these genes may also be inserted into the expression vector at the 3'-end of the sequence which is to be expressed, in order to ensure polyadenylation and termination of the mRNA.

Other promoters which also have the advantage of transcription controlled by growth conditions are the promoter regions of the genes for alcohol dehydrogenase-2, isocytochrome C, acid phosphatase, degradation enzymes which are coupled to nitrogen metabolism, the above-mentioned glyceraldehyde-3-phosphate dehydrogenase and enzymes which are responsible for the processing of maltose and galactose. Promoters which are regulated by the yeast mating type locus, for example promoters of the genes BAR1, MFα1, STE2, STE3 and STE5, may be used in temperature-regulated systems by the use of temperature-dependent sir mutations (Rhine, Ph.D. Thesis, University of Oregon, Eugene, Oregon (1979), Herskowitz and Oshima, The Molecular Biology of the Yeast Saccharomyces, Part I, 181–209 (1981), Cold Spring Harbour Laboratory)). These mutations affect the expression of the resting mating type cassettes of yeasts and thus indirectly the mating type dependent promoters. Generally, however, any plasmid vector which contains a yeast-compatible promoter, origin of replication and termination sequences, is suitable.

In addition to microorganisms, cultures of multicellular organisms are also suitable host organisms. In theory, any of these cultures may be used, whether obtained from vertebrate or invertebrate animal cultures. However, the greatest interest has been in vertebrate cells, with the result that the multiplication of vertebrate cells in culture (tissue culture) has become a routine method in recent years (Tissue Culture, Academic Press, Editors Kruse and Patterson, (1973)). Examples of useful host cell lines of this kind include VERO and HeLa cells, CHO cells and WI38, BHK, COS-7 and MDCK cell lines. Expression vectors for these cells generally contain (when necessary) a replication site, a promoter which is located in front of the gene to be expressed, together with any necessary ribosome binding site, RNA splicing site, polyadenylation site and transcriptional termination sequences.

When used in mammalian cells, the control functions in the expression vector are often obtained from vital material. For example, the promoters normally used originate from polyoma adenovirus 2 and particularly frequently from Simian virus 40 (SV 40). The early and late promoters of SV 40 are particularly useful since both can be easily obtained from the virus as a fragment which also contains the vital replication site of the SV 40 (Fiers et al., Nature 273, 113 (1978)). It is also possible to use smaller or larger fragments of SV 40, provided that they contain the sequence, approximately 250 bp long, which extends from the HindIII cutting site to, the Bgl1 cutting site in the vital replication site. Furthermore it is also possible and often desirable to use promoter or control sequences which are normally linked to the desired genetic sequences, provided that these control sequences are compatible with the host cell systems.

A replication starting point may either be provided by corresponding vector construction in order to incorporate an exogenic site, for example from SV 40 or other vital sources (e.g. polyoma, adeno, VSV, PBV, etc.) or it may be provided by the chromosomal replication mechanisms of the host cell. If the vector is integrated into the host cell chromosome, the latter measure is usually sufficient.

Preferably, the DNA sequences according to the invention may also be expressed in the expression plasmid pER103 (E. Rastl-Dworkin et al., Gene 21, 237–248 (1983) and EP-A-0115613—deposited at the DSM under No. DSM 2773 on 20th Dec. 1983), in the plasmid parpER33 (EP-A-0115613) or the plasmid pRH100, since these vectors all contain regulatory elements which lead to a high express ion rate for the cloned genes. According to the invention, the plasmid pRH100 which contains the regulatable tryptophan promoter from *Serratia marcescens* and an artificial ribosome binding site, is used as the expression vector for the synthetic EqIFN-γ gene. In order to prepare the expression plasmid pRH100, the plasmid pER103 (Eva Dworkin-Rastl et al., Gene 21 (1983) 237–248, EP-A-0115613) was linearised with the restriction endonuclease HindIII and the 5' terminal phosphate residues were removed.

This plasmid DNA was mixed and ligated with the phosphorylated oligonucleotides d(AGCTTAAAGATGAGCT) and d(CATCTTTA). The ligase reaction was digested with the restriction endonuclease SacI and ligated by addition of T4-PNK. The oligonucleotides were prepared analogously to the method described in EP-A-0115613. Competent *E. coli* HB101 were mixed with this ligase reaction and incubated. Of the resulting colonies of bacteria, 12 were selected at random and the plasmids were isolated therefrom on a microscopic scale (Birnboim and Doly, Nucl. Acids Res. 7 (1979) 1513–1523). The resulting DNA was cut with the restriction endonuclease SacI and the DNA was separated on an agarose gel (1%, 1×TBE buffer). The migration of the DNA as a linear molecule of a magnitude of about 4,400 bp confirmed the insertion of a SacI recognition site into the plasmid. One of these plasmids was selected at random. *E. coli* HB101 was again transformed with the DNA from the associated mini-preparation. Of the resulting transformed bacteria, one colony was selected and cultivated on a larger scale. The plasmid isolated therefrom was cut with the restriction endonucleases EcoRI and BamHI, the DNA was separated on a 1% agarose gel and the smaller fragment was isolated from the gel by electroelution. This EcoRI-BamHI DNA fragment, about 460 bp long, was sequenced according to Sanger (F. Sanger et al., Proc. Natl. Acad. Sci. (1977) 5463–5467). The plasmid thus analysed was designated pRH100.

The plasmid was totally cut with SacI and the overhanging DNA ends were straightened by treatment with Klenow fragment (Amersham) in the presence of all four deoxynucleotide triphosphates. The reaction is stopped by extraction with phenol/chloroform and the DNA is concentrated by ethanol precipitation. This treatment results in a blunt DNA end adjoining the trytophan promoter and ending with the translation start codon "ATG". The linearised plasmid DNA is cut again with BamHI and the vector fraction is isolated.

The pRH100 plasmid vector thus prepared is mixed with the ligated oligonucleotides EG-1 to EG-8 and EG-9 to EG-14 and incubated in ligation buffer with T4 DNA ligase. *E. coli*, preferably JM101, which has been made competent, is transformed with this ligation mixture and incubated overnight. From the transformants obtained, plasmid DNA is isolated by the mini-preparation method and the structure is determined by restriction analysis and sequencing the HindIII-BamHI inserts. A plasmid of the desired structure for expressing mature EqIFN-γ is designated pEqG-YYC1. In totally analogous manner, the oligonucleotides EG-15,16, EG-3 to EG-8 and EG-9 to EG-14 are cloned into the pRH100 vector in order to obtain the EqIFN-γ shortened by three amino acids. A plasmid of the desired structure is designated pEqG-QAA1.

Transformation of the cells with the vehicles can be achieved by a number of processes. For example, it can be effected using calcium, either by washing the cells in magnesium and adding the DNA to the cells suspended in calcium or by subjecting the cells to a coprecipitate of DNA and calcium phosphate. During the subsequent gene expression, the cells are transferred to media which select for transformed cells.

In order to detect the expression of interferon activity by *E. coli* JM101 which contain the plasmid pEqG-YYC1 or pEqG-QAA1, after incubation in a suitable culture medium, the bacteria are broken up and the supernatant, having been sterile filtered, is tested for interferon activity in an assay which measures the cytopathic effect (CPE) of VSV or EMCV. NBL-6 cells (ATCC CCL 57, horse hide epidermis cells) which had been infected with vesicular stomatitis virus (VSV) and/or A549 (ATCC CCL185, human lung cancer cell line) which had been infected with encephalomyocarditis virus (EMCV) are used for this purpose.

The expressed horse interferons are detected by labelling the proteins in maxi-cells. Plasmid-coded proteins may be labelled selectively in vivo using the maxi-cell technique (Sancar, A. et al., J. Bacteriol, 137, 692–693 (1979). The *E. coli* strain CSR603 (CGSC 5830) has no mechanisms for the repair of damage caused to the DNA by UV radiation. Irradiation with a suitable dosage of UV rays destroys the bacterial chromosome, but some of the substantially smaller plasmid DNAs which are present in several copies per cell remain functional. After all the undamaged replicating cells have been killed off by the antibiotic D-cycloserine and the endogenous mRNA has been used up, only genes still coded on the plasmid are transcribed and translated in the remaining cells. The proteins formed may be radio-actively labelled and detected by the introduction of $^{35}$S-methionine. *E. coli* CSR603 is transformed with the expression plasmids by conventional methods and selected on ampicillin-containing agar dishes for transformed bacteria. The preparation of the maxi-cells and the labelling of the proteins are carried out using the method described by A. Sancar. A $^{14}$C-methylated protein mixture (Amersham) is used as the molecular weight standard. The controls used are the plasmid pER103 which contains only the promoter without any interferon gene and the plasmid pER21/1, which contains two copies of the human IFN-α2arg gene.

The products according to the invention may conveniently be characterised by the known biological and immunological assays for interferons. Since IFN-α, -β and -γ all have the antiviral property which can be detected in the PFU and CPE assays, the difference in the antigenicity of the interferons is used to distinguish the EqIFN-γ's according to the invention from EqIFN-α and/or β.

The polypeptides according to the invention are not neutralised by antisera against EqIFN-α and/or EqIFN-β. A further distinguishing criterion is the acid lability of the polypeptides according to the invention and their sensitivity to sodium dodecylsulphate (SDS). Both incubation with 0.2% SDS solution and also incubation of the polypeptides at $pH_2$ for several hours at 4° C. results in an almost complete loss of antiviral activity. EqIFN-α and EqIFN-β are stable under the same conditions.

In order to detect the total number of sequences in the horse genome which have high homology with the interferon gene, high molecular weight horse DNA is totally digested with the corresponding restriction enzymes and this cut DNA is divided up according to size. After Southern transfer onto nitrocellulose filters, denaturing and fixing the DNA, each filter is hybridised with nick-translated probe. The probe used for EqIFN-γ is a fragment of the plasmid pEqG-YYC1 which contains the coding sequence for the entire mature interferon. The filters are then washed under stringent conditions. Autoradiography is carried out on DuPont Cronex X-ray film using Kodak Lanex-Regular Intensifier film over a period of 7 days at −80° C.

After transformation of the host, expression of the gene and fermentation or cell cultivation under conditions in which the proteins according to the invention are expressed, the product can usually be extracted by known chromatographic methods of separation, so as to obtain a material which contains the proteins with or without leader and tailing sequences. The interferons according to the invention may be expressed with a leader sequence at the N terminus (pre-IFN), which can be removed by some host cells. If not, the leader polypeptide (if present) must be cleaved in order to obtain mature IFN. Alternatively, the IFN clone may be modified so that the mature protein is produced directly in the microorganism instead of the pre-IFN. In this case, the precursor sequence of the yeast mating pheromone MF-alpha-1 may be used to ensure correct "maturation" of the fused protein and secretion of the products into the growth medium or the periplasmic space. The DNA sequence for functional or mature IFN may be linked to MF-alpha-1 at the supposed kathepsin-like cutting site (after Lys-Arg) at position 256 starting from the initiation codon ATG (Kurjan, Herskowitz, Cell 30, 933–943 (1982)).

A method by which EqIFN-γ can be purified, for example from bacteria, is described in the following general plan.

1. Extraction of the cells in a lysis buffer (approx. pH 8) of high conductivity by passing through a homogeniser under high pressure; the discharge current being cooled in an ice bath.
2. Precipitation of the DNA by the addition of polyethyleneimine with stirring, e.g. at 4° C.
3. pH precipitation of the bacterial proteins, EqIFN-γ again remaining in solution.
4. Removal of the solids by centrifuging at 4° C.
5. Concentration of the supernatant (after readjustment of the pH) e.g. by ultrafiltration.
6. Dialysis of the concentrate against a buffer of low conductivity.
7. Removal of the solids by centrifuging, EqIFN-γ remaining in solution.
8. Ion exchange chromatography on carboxymethylcellulose, elution with a gradient of increasing
9. Chromatography on calcium phosphate gel and elution with a gradient of increasing ionic strength.
10. Ion exchange chromatography on carboxymethylcellulose under slightly denaturing conditions and elution with a gradient of increasing ionic strength.
11. Separation by gel filtration chromatography.

The process described results in material yields with a purity of more than 95%.

At this point it should be mentioned that the interferons according to the invention are not only the interferons described in detail but also any modifications of these peptides which do not substantially alter the horse γ-IFN activity. These modifications include, for example, shortening of the molecule, e.g. at the N or C terminal end, the substitution of amino acids by other groups, chemical or biochemical binding of the molecule to other molecules which are inert or active. The latter modifications may, for example, involve hybrid molecules from one or more interferons according to the invention and/or known α- or β-interferons.

On the basis of their biological spectrum of activity, the new interferons according to the invention may be used for any type of treatment for which known interferons are also used. These include, for example, herpes, rhinovirus, equine abortion virus, various types of cancer and the like. The new interferons may be used on their own or in conjunction with other known interferons or biologically active products, for example IFN-α, IL-2, other immune modulators and the like.

The interferons according to the invention may be administered by parenteral route in cases where antitumour or antiviral treatment is required and in cases in which immunosuppressant properties are apparent. The dosage and dosage rate may be similar to those currently used for IFN materials in clinical trials, e.g. approximately $(1–10)\times10^6$ units per day and, in the case of preparations with a purity of more than 1%, up to $5\times10^7$ units per day.

As an example of a convenient dosage form for a substantially homogeneous, bacterially produced IFN according to the invention, for parenteral use 3 mg of EqIFN-γ are dissolved in 25 ml of 5% animal serum albumin, preferably horse/dog serum albumin. This solution is then passed through a bacteriological filter and the filtered solution is aseptically divided between 100 vials, each of which contains $6\times10^6$ units of pure IFN suitable for parenteral administration. Before use, the vials are preferably stored in the cold (−20° C.). The substances according to the invention may be formulated in known manner to obtain compositions suitable for pharmaceutical use, the polypeptide according to the invention being mixed with a pharmaceutically acceptable carrier substance. Suitable carrier substances and their formulation are described by E. W. Martin in Remingtom's Pharmaceutical Sciences, to which reference is expressly made. The interferons according to the invention are mixed with a suitable amount of the carrier in order to obtain pharmaceutical compositions suitable for effective administration to the receiver (patient). Parenteral administration is preferred.

This invention further relates to monoclonal antibodies against the polypeptides according to the invention, hybridoma cells which produce such antibodies and processes for preparing them. Hybridoma cell lines and the monoclonal antibodies secreted by them which react specifically with EqIFN-gamma are preferred. The process for preparing such monoclonal antibodies is characterised in that small mammals, for example rabbits or mice, are immunised with the polypeptides according to the invention, B-lymphocytes of these immunised animals are fused with myeloma cells, the hybridoma cells formed are cloned, then cultivated in vitro or by injection into mice and antibodies are isolated from the cultures.

The invention further relates to immuno-affinity chromatography columns and test kits for immunoassays which contain these antibodies.

Using the process according to the invention, mice, e.g. Balb/c mice, are immunised in a manner known per se. In a preferred embodiment, the polypeptides according to the invention are injected more or less weekly or possibly at longer intervals over a period of several weeks, for example 5 to 12 weeks, until a sufficient number of antibody-producing B-lymphocytes has formed.

Organs which contain B-lymphocytes, e.g. spleen cells, from the immunised mice are taken and fused with myeloma cells which, as a result of a mutation, do not grow in a selective culture medium. These myeloma cells are known and may be, for example, those designated X63-Ag8, X63-Ag8.6.5.3, MPC-11, NSl-Ag4/1, MOPC-21 NS/1 or SP 2/0. In a preferred embodiment, spleen cells from immunised mice are fused with myeloma cells of the cell line X63-Ag8.6.5.3. The fusion is carried out by methods known per se by mixing the B-lymphocytes and the myeloma cells with the addition of a cell fusion agent such as polyethylene glycol, Sendai virus, calcium chloride or lysolecithin. Preferably, the fusion is carried out in the presence of polyethylene glycol, for example with a molecular weight of between 1000 and 4000. After the fusion, the resulting hybrids are cultivated by a method known per se in a selective culture medium which is supplemented with hypoxanthine, aminopterin and thymidine (HAT medium). Non-fused myeloma cells cannot grow in this medium and die, as do normal lymphocytes.

The supernatants from the hybridoma cultures may be tested for their content of specific antibodies by known methods, for example by radioimmunoassay or agglutination. The hybridoma cells which produce antibodies of the desired specificity are selected by cloning the mixture of various hybridoma cells produced by the fusion. To do this, cultures are initiated from a single growing cell using a method known per se, referred to as "limiting dilution".

For mass production, the hybridoma cell clones which produce antibodies of the desired specificity are either cultivated in vitro in media known per se or are injected into mice for replication. In a preferred embodiment, hybridoma cells are injected into mice which have been pretreated with pristane, ascitic fluid is taken and antibodies are isolated therefrom by precipitation with ammonium sulphate solution.

The specific antibodies obtained using these hybridoma cells may be used in a manner known per se for the production of immuno-affinity chromatography columns. In a preferred embodiment of the invention, a suitable carrier material (suspended in a buffer solution) is combined with an antibody solution, any unbound parts are subsequently washed out and unoccupied parts of the carrier material are blocked. The antibodies may also be used in therapy.

The specific antibodies obtained using the hybridoma cells may be used in a manner known per se to produce test kits. These test kits may be based on various methods, e.g. radioimmunoassay, latex agglutination, spot tests, competitive or sandwich radioimmunoassay, enzyme immunoassay, immunofluorescence or immunochemical enzyme tests.

SUMMARY OF THE INVENTION

The invention relates in particular to:

Polypeptides in a substantially pure form
- with the biological and immunological properties of horse interferon-gamma (EqIFN-gamma);
- substantially free from other proteins of animal origin;
- free from native glycosylation;
- containing the amino acid methionine before the first amino acid of the N-terminus;
- containing a leader peptide;
- containing the amino acid sequence

| | | | | | | | | | | | | | | |
|---|---|---|---|---|---|---|---|---|---|---|---|---|---|---|
| 1 | | | | 5 | | | | | 10 | | | | | 15 |
| Tyr | Tyr | Cys | Gln | Ala | Ala | Phe | Phe | Lys | Glu | Ile | Glu | Asn | Leu | Lys |
| | | | | 20 | | | | | 25 | | | | | 30 |
| Glu | Tyr | Phe | Asn | Ala | Arg | Asn | Pro | Asp | Val | Gly | Asp | Gly | Gly | Pro |
| | | | | 35 | | | | | 40 | | | | | 45 |
| Leu | Phe | Leu | Asp | Ile | Leu | Lys | Asn | Trp | Lys | Glu | Asp | Ser | Asp | Lys |
| | | | | 50 | | | | | 55 | | | | | 60 |
| Lys | Ile | Ile | Gln | Ser | Gln | Ile | Val | Ser | Phe | Tyr | Phe | Lys | Leu | Phe |
| | | | | 65 | | | | | 70 | | | | | 75 |
| Glu | Asn | Leu | Lys | Asp | Asn | *Gln | Val | Ile | Gln | Lys | Ser | Met | Asp | Thr |

-continued

| | | | | | | | | | | | | | | |
|---|---|---|---|---|---|---|---|---|---|---|---|---|---|---|
| | | | | 80 | | | | | 85 | | | | | 90 |
| Ile | Lys | Glu | Asp | Leu | Phe | Val | Lys | Phe | Phe | Asn | Ser | Ser | Thr | Ser |
| | | | | 95 | | | | | 100 | | | | | 105 |
| Lys | Leu | Glu | Asp | Phe | Gln | Lys | Leu | Ile | Gln | Ile | Pro | Val | Asn | Asp |
| | | | | 125 | | | | | 130 | | | | | 135 |
| Asn | Asp | Leu | Ser | Pro | Lys | Ala | Asn | Leu | Arg | Lys | Arg | Lys | Arg | Ser |
| | | | | 140 | | | | | 145 | | | | | |
| Gln | Asn | Pro | Phe | Arg | Gly | Arg | Arg | Ala | Leu | Gln *** | | | | |

or

| | | | | | | | | | | | | | | |
|---|---|---|---|---|---|---|---|---|---|---|---|---|---|---|
| | | | Gln | Ala | Ala | Phe | Phe | Lys | Glu | Ile | Glu | Asn | Leu | Lys |
| Glu | Tyr | Phe | Asn | Ala | Arg | Asn | Pro | Asp | Val | Gly | Asp | Gly | Gly | Pro |
| Leu | Phe | Leu | Asp | Ile | Leu | Lys | Asn | Trp | Lys | Glu | Asp | Ser | Asp | Lys |
| Lys | Ile | Ile | Gln | Ser | Gln | Ile | Val | Ser | Phe | Tyr | Phe | Lys | Leu | Phe |
| Glu | Asn | Leu | Lys | Asp | Asn | Gln | Val | Ile | Gln | Lys | Ser | Met | Asp | Thr |
| Ile | Lys | Glu | Asp | Leu | Phe | Val | Lys | Phe | Phe | Asn | Ser | Ser | Thr | Ser |
| Lys | Leu | Glu | Asp | Phe | Gln | Lys | Leu | Ile | Gln | Ile | Pro | Val | Asn | Asp |
| Leu | Lys | Val | Gln | Arg | Lys | Ala | Ile | Ser | Glu | Leu | Ile | Lys | Val | Met |
| Asn | Asp | Leu | Ser | Pro | Lys | Ala | Asn | Leu | Arg | Lys | Arg | Lys | Arg | Ser |
| Gln | Asn | Pro | Phe | Arg | Gly | Arg | Arg | Ala | Leu | Gln *** | | | | |

DNA molecules coding for a polypeptide with the biological and immunological properties of EqIFN-gamma;

for a polypeptide as referred to above;

for mature EqIFN-gamma.

DNA molecules containing the complete natural gene for EqIFN-gamma;

containing the nucleotides

ATG AAT TAT ACA AGT TTT ATC TTG GCT TTT CAG CTG TGT GCG ATT

TTG GGT TCT TCT ACC TAT TAC TGC CAG GCC GCG TTT TTT AAA GAA

----------- INTRON 1 ---------------

ATA GAA AAC CTA AAG GAA TAT TTT GTAAGTATGACCTTTTAATAATACTTAC

TTGTGGTTGAAATGACTGAACGTTGTCTTGGAGTTGGATCTCTGATAGGCTGTCCTCTCT

ACTCCACAGTCATCTTGAGAAGACTGGGTGTTATTTTCTCTGTTTGTTGACTGGATGAGT

TTTTCTTTTTTTTACTAAATGATCTAGATATTGCTTTAACCCTCTGCTCAATTTGCTATA

GAGACTTAGAGAGGGTTCATGAATCTTCCAAAAGATGGGCTTAACAGGTTTATAAAGCAT

AGTGAAGTTGACAATTTTGTGGTGAGAAGCCACTGAATTGTGATAAGTCAAGTAGTGTGG

ACATTGAAAAAATGACTAGCTATTAGTTTCTAACTTCTCAGGTTACTATGATGGTGACAA

TAAAAGGTCAAGATTAGCATTAAAATGGTAATCTGAAATAATTGATCAGTTAAAGAAGGC

GCTGTCCTGAAAGGTTTGGCTGAAAAAAAATCACTTTCAGGTGTTTTCCTCCAAAAAATG

ATTTTAAAATCTTACTGCCCCGTTTGTGTTAGCTGTGAAGTACTCTGGAACTCAGTCAAT

TGCTGAGATTTTGTACGAGTTATAAGCTGGCTTATATTTAAAAAATTTTTTTGTTTTTGT

TTTATGAGTTTCTTTTAAAATGTTATTTATGGTTAATTAAAATAGTTTTTGCATTTTAAA

TATTTTATTATTTGTCCAAAATTTAGCTATTTTAATTATAGTTGGAGCTCTCTTTTAGAG

CTGACATAAGACCATAGGGGAGGCACAGATAGATGTGATGGAGCCCTGTACCAGACGGGG

GCAGTATCTTATAGTGGGTTGCCTTTGCTGATCTTTTTACTAGACTTGAAATTATTTGCT

TTTCCTTCCTATGGTTATTTGGGACTATTGAAGTATCACCAGCCCTGTTGAGTTCATCTG

TAATATTGTAATTCAAGGGTTACACTAGAAAATAAGAAAGCTAAAACAGCACGATAATCT

TTGGCTACATCCAACACAATAGCTTTTGGGAATACTTATTGTTAGAACTAAACAGAGGGT

TGAAAAGAAAATCAGTGAATACTGTCAGCATCTGAGTTCAATAAAACGTGAAGTACATTT

---------------------------------------------------
TTAGGGCAATTCATGGACTAATTGTAAACCAAGTTTTCCTTCCTTTTTCAG AAC GCA

AGA AAC CCA GAT GTA GGG GAT GGT GGG CCT CTT TTC CTG GAT ATC

--------------------------- INTRON 2 –
TTG AAG AAC TGG AAA GAG GTAAGCTAAGTATTTCCATTTGGTTGATTTTCCTGT
-------------------------------------------------------------
TGCTTATTTTCTGGTGGATGAATTCACACCAACCTCTCTTTGTGCTCTTTTCTCCCTAG

GAT AGT GAC AAA AAA ATA ATT CAG AGC CAA ATC GTC TCC TTC TAC

TTC AAA CTC TTT GAA AAC TTG AAA GAT AAC CAG GTC ATT CAA AAG

AGC ATG GAC ACC ATC AGG GAG GAC CTG TTC GTT AAG TTC TTT AAC

AGC AGC ACC AGC AAG CTG GAA GAC TTC CAA AAG CTG ATT CAG ATT

----------- INTRON 3 ----------------------------------
CCG GTGAGGAGATCTTAATTCTTTCTTTGGTTTCATTACAGAGGTTCTTGCAAAGTGCT

TACGTCCCAGAAAGTAGAAATGAACTATGAAATGAACCCGTGGCCAAAACTCCTCCTTCC

TAATTCCATTTGTGCTTTGAGAGACTTTGCTAAGTCAGTATGGGAATCATTTAAATTTGT

GATTTGGGGAAATGCTGGCACTATGACTACTGCACAAAGGCAGGTGAAGGGACAAATCCA

GTGAGGAGGGGGCAGTGAAGAAGTGGAGGGGAGTCTGGAGAAGCAGGTCTCTCCTTGCCC

CTTGTTCGTGAGATGAAATCCTCCTGCTTTGGATGGGAGGCTGCGTGTCTTGGTGGAAAG

AGCAGTGGGAGGAGGGAGAAGATTTGTGCTCCTCCCAGCTCAGCCACCAAGAAACTGTGA

CCTCAGATGAATCACAGGCCTGGCTGGGGCTCAGTTTCCTCATCTTAAAAGAGGCCTATT

GGGTTCACTAAAATTTCTATGATCTTCTTTGCTCTATAATCCTACAATTCTGTGGACAGA

AAATGAAATGAGGTAGGAGAAAGAAATAGCCTTTGAAGAGGTTCTTGGGCATTCCACTGC

CAGGCTCTGGTCAACCTTCATACTCTGCAGCCCAAGAAGAGGCAAGACCATTTGTCTGTT

TTTGGAAATGCAAATAGGCGGCATTTATACCTCACGAAAGAACTGTTCTGTCAACTTTTG

GATACTGGGCTATCTTGGCTGGAGAAATCCTTAGGCTCCCAAACTTTCTCTCATGAAATT

GTCTTGAGTCTTTAAATTTATGGCTTCTCGAAGCTGAGAGATAACTTTAAGCATAAAGAC

AAATTACATTTTCCAACATTTTGTCTAAGAGACAAAGACCTCCACATGCCTTTGGGTTTG

GCCTGGATCTAAATGGGCTTGAATGAGAAGGGGAGGGTGTTGTTATGACTATGTTTAGAA

GAGAAAACAGAGGTTTGGAGAGGTTAAGTGGCTGGTTCAAAGTCAGAGTTATTGCACACA

CAGGATTCGAACCCATATGTTTTGTCCCTCCACTTTAGGGTTCTTTTCGCTACATAATTT

TGAGAATTCTGTACCAGTCAATTTAAGGATGTGTGATGTTCCCCATCCTATTACAGCACA

ACCAGCAATTTAATTATAATTTTAGTCTTAACTGCTGAAGAAAGCAGCATTACATATTAA

GCTAACATATTCCTGGTGAAAGCAACTTTTTCAAAGGAATATTTCTATTTTCATGGACCA

TGACAGTAGCACAGCCTGATGGCTTGTATGCCTGAAACTAATTTTGCTGTTTTCTTTCCC
-----
AATAG GTA AAT GAT CTG AAG GTC CAG CGC AAA GCA ATA AGT GAA CTC

ATC AAA GTG ATG AAT GAT CTG TCG CCC AAA GCT AAC CTG AGG AAG

-continued

CGG AAG AGG AGT CAG AAT CCA TTT CGA GGC CGG AGA GCG TTG CAA

***
TAG or

TAT TAC TGC CAG GCC GCG TTT TTT AAA GAA

----- INTRON 1 -----------------

ATA GAA AAC CTA AAG GAA TAT TTT GTAAGTATGACCTTTTAATAATACTTAC

TTGTGGTTGAAATGACTGAACGTTGTCTTGGAGTTGGATCTCTGATAGGCTGTCCTCTCT

ACTCCACAGTCATCTTGAGAAGACTGGGTGTTATTTTCTCTGTTTGTTGACTGGATGAGT

TTTTCTTTTTTTTACTAAATGATCTAGATATTGCTTTAACCCTCTGCTCAATTTGCTATA

GAGACTTAGAGAGGGTTCATGAATCTTCCAAAAGATGGGCTTAACAGGTTTATAAAGCAT

AGTGAAGTTGACAATTTTGTGGTGAGAAGCCACTGAATTGTGATAAGTCAAGTAGTGTGG

ACATTGAAAAAATGACTAGCTATTAGTTTCTAACTTCTCAGGTTACTATGATGGTGACAA

TAAAAGGTCAAGATTAGCATTAAAATGGTAATCTGAAATAATTGATCAGTTAAAGAAGGC

GCTGTCCTGAAAGGTTTGGCTGAAAAAAAATCACTTTCAGGTGTTTTCCTCCAAAAAATG

ATTTTAAAATCTTACTGCCCCGTTTGTGTTAGCTGTGAAGTACTCTGGAACTCAGTCAAT

TGCTGAGATTTTGTACGAGTTATAAGCTGGCTTATATTTAAAAAATTTTTTTGTTTTTGT

TTTATGAGTTTCTTTTAAAATGTTATTTATGGTTAATTAAAATAGTTTTTGCATTTTAAA

TATTTTATTATTTGTCCAAAATTTAGCTATTTTAATTA TAGTTGGAGCTCTCTTTTAGAG

CTGACATAAGACCATAGGGGAGGCACAGATAGATGTGATGGAGCCCTGTACCAGACGGGG

GCAGTATCTTATAGTGGGTTGCCTTTGCTGATCTTTTTACTAGACTTGAAATTATTTGCT

TTTCCTTCCTATGGTTATTTGGGACTATTGAAGTATCACCAGCCCTGTTGAGTTCATCTG

TAATATTGTAATTCAAGGGTTACACTAGAAAATAAGAAAGCTAAAACAGCACGATAATCT

TTGGCTACATCCAACACAATAGCTTTTGGGAATACTTATTGTTAGAACTAAACAGAGGGT

TGAAAAGAAAATCAGTGAATACTGTCAGCATCTGAGTTCAATAAAACGTGAAGTACATTT

---------------------------------------------------------------

TTAGGGCAATTCATGGACTAATTGTAAACCAAGTTTCCTTCCTTTTTCAG AAC GCA

AGA AAC CCA GAT GTA GGG GAT GGT GGG CCT CTT TTC CTG GAT ATC

------------------------------ INTRON 2 -

TTG AAG AAC TGG AAA GAG GTAAGCTAAGTATTTCCATTTGGTTGATTTTCCTGT

---------------------------------------------------------------

TGCTTATTTTCTGGTGGATGAATTCACACCAACCTCTCTTTGTGCTCTTTTCTCCCTAG

GAT AGT GAC AAA AAA ATA ATT CAG AGC CAA ATC GTC TCC TTC TAC

TTC AAA CTC TTT GAA AAC TTG AAA GAT AAC CAG GTC ATT CAA AAG

AGC ATG GAC ACC ATC AAG GAG GAC CTG TTC GTT AAG TTC TTT AAC

AGC AGC ACC AGC AAG CTG GAA GAC TTC CAA AAG CTG ATT CAG ATT

----------- INTRON 3 ----------------------------------------

CCG GTGAGGAGATCTTAATTCTTTCTTTGGTTTCATTACAGAGGTTCTTGCAAAGTGCT

TACGTCCCAGAAAGTAGAAATGAACTATGAAATGAACCCGTGGCCAAAACTCCTCCTTCC

TAATTCCATTTGTGCTTTGAGAGACTTTGCTAAGTCAGTATGGGAATCATTTAAATTTGT

GATTTGGGGAAATGCTGGCACTATGACTACTGCACAAAGGCAGGTGAAGGGACAAATCCA

GTGAGGAGGGGGCAGTGAAGAAGTGGAGGGGAGTCTGGAGAAGCAGGTCTCTCCTTGCCC

CTTGTTCGTGAGATGAAATCCTCCTGCTTTGGATGGGAGGCTGCGTGTCTTGGTGGAAAG

AGCAGTGGGAGGAGGGAGAAGATTTGTGCTCCTCCCAGCTCAGCCACCAAGAAACTGTGA

-continued

CCTCAGATGAATCACAGGCCTGGCTGGGGCTCAGTTTCCTCATCTTAAAAGAGGCCTATT
GGGTTCACTAAAATTTCTATGATCTTCTTTGCTCTATAATCCTACAATTCTGTGGACAGA
AAATGAAATGAGGTAGGAGAAAGAAATAGCCTTTGAAGAGGTTCTTGGGCATTCCACTGC
CAGGCTCTGGTCAACCTTCATACTCTGCAGCCCAAGAAGAGGCAAGACCATTTGTCTGTT
TTTGGAAATGCAAATAGGCGGCATTTATACCTCACGAAAGAACTGTTCTGTCAACTTTTG
GATACTGGGCTATCTTGGCTGGAGAAATCCTTAGGCTCCCAAACTTTCTCTCATGAAATT
GTCTTGAGTCTTTAAATTTATGGCTTCTCGAAGCTGAGAGATAACTTTAAGCATAAAGAC
AAATTACATTTTCCAACATTTTGTCTAAGAGACAAAGACCTCCACATGCCTTTGGGTTTG
GCCTGGATCTAAATGGGCTTGAATGAGAAGGGGAGGGTGTTGTTATGACTATGTTTAGAA
GAGAAAACAGAGGTTTGGAGAGGTTAAGTGGCTGGTTCAAAGTCAGAGTTATTGCACACA
CAGGATTCGAACCCATATGTTTTGTCCCTCCACTTTAGGGTTCTTTTCGCTACATAATTT
TGAGAATTCTGTACCAGTCAATTTAAGGATGTGTGATGTTCCCCATCCTATTACAGCACA
ACCAGCAATTTAATTATAATTTTAGTCTTAACTGCTGAAGAAAGCAGCATTACATATTAA
GCTAACATATTCCTGGTGAAAGCAACTTTTTCAAAGGAATATTTCTATTTTCATGGACCA
TGACAGTAGCACAGCCTGATGGCTTGTATGCCTGAAACTAATTTTGCTGTTTTCTTTCCC

-----
AATAG GTA AAT GAT CTG AAG GTC CAG CGC AAA GCA ATA AGT GAA CTC
ATC AAA GTG ATG AAT GAT CTG TCG CCC AAA GCT AAC CTG AGG AAG
CGG AAG AGG AGT CAG AAT CCA TTT CGA GGC CGG AGA GCG TTG CAA
***
TAG or 1 5 10 15
TAT TAC TGC CAG GCC GCG TTT TTT AAA GAA ATA GAA AAC CTA AAG
20 25 30
GAA TAT TTT AAC GCA AGA AAC CCA GAT GTA GGG GAT GGT GGG CCT
35 40 45
CTT TTC CTG GAT ATC TTG AAG AAC TGG AAA GAG GAT AGT GAC AAA
50 55 60
AAA ATA ATT CAG AGC CAA ATC GTC TCC TTC TAC TTC AAA CTC TTT
65 70 75
GAA AAC TTG AAA GAT AAC CAG GTC AAT CAA AAG AGC ATG GAC ACC
80 85 90
ATC AAG GAG GAC CTG TTC GTT AAG TTC TTT AAC AGC AGC ACC AGC
95 100 105
AAG CTG GAA GAC TTC CAA AAG CTG ATT CAG ATT CCG GTA AAT GAT
110 115 120
CTG AAG GTC CAG CGC AAA GCA ATA AGT GAA CTC ATC AAA GTG ATG
125 130 135
AAT GAT CTG TCG CCC AAA GCT AAC CTG AGG AAG CGG AAG AGG AGT
140 145
CAG AAT CCA TTT CGA GGC CGG AGA GCG TTG CAA TAG or

−1 1 5 10 15
ATG TAC TAC TGC CAG GCT GCT TTC TTT AAA GAA ATC GAA AAC CTG AAA
20 25 30
GAA TAC TTC AAC GCT CGT AAC CCA GAC GTT GGT GAC GGT GGT CCG
35 40 45
CTG TTC CTG GAC ATC CTG AAA AAC TGG AAA GAA GAC TCT GAC AAA

-continued

```
                50                  55                  60
AAG ATC ATC CAG TCT CAG ATC GTT TCT TTC TAC TTC AAA CTG TTC

                65                  70                  75
GAA AAC CTG AAA GAC AAC CAG GTT ATC CAG AAA TCG ATG GAC ACT

                80                  85                  90
ATC AAA GAA GAT CTG TTC GTT AAA TTC TTC AAC TCG TCG ACT TCT

                95                  100                 105
AAA CTG GAA GAC TTC CAG AAA CTG ATC CAG ATC CCA GTT AAC GAC

                110                 115                 120
CTG AAA GTT CAG CGT AAG GCT ATC TCT GAA CTG ATC AAA GTT ATG

                125                 130                 135
AAC GAC CTG TCT CCA AAA GCT AAC CTG CGT AAA CGT AAA CGT TCT

                140                 145
CAG AAC CCA TTC CGT GGT CGT CGT GCT CTT CAG TAA
```

or

```
 -1  1              5                  10                  15
ATG CAG GCT GCT TTC TTT AAA GAA ATC GAA AAC CTG AAA GAA TAC TTC

                20                  25                  30
AAC GCT CGT AAC CCA GAC GTT GGT GAC GGT GGT CCG CTG TTC CTG

                35                  40                  45
GAC ATC CTG AAA AAC TGG AAA GAA GAC TCT GAC AAA AAG ATC ATC

                50                  55                  60
CAG TCT CAG ATC GTT TCT TTC TAC TTC AAA CTG TTC GAA AAC CTG

                65                  70                  75
AAA GAC AAC CAG GTT ATC CAG AAA TCG ATG GAC ACT ATC AAA GAA

                80                  85                  90
GAT CTG TTC GTT AAA TTC TTC AAC TCG TCG ACT TCT AAA CTG GAA

                95                  100                 105
GAC TTC CAG AAA CTG ATC CAG ATC CCA GTT AAC GAC CTG AAA GTT

                110                 115                 120
CAG CGT AAG GCT ATC TCT GAA CTG ATC AAA GTT ATG AAC GAC CTG

                125                 130                 135
TCT CCA AAA GCT AAC CTG CGT AAA CGT AAA CGT TCT CAG AAC CCA

                140             143
TTC CGT GGT CGT CGT GCT CTT CAG TAA
```

and optionally additionally containing the leader sequence

ATG AAT TAT ACA AGT TTT ATC TTG GCT TTT CAG CTG TGT GCG ATT

TTG GGT TCT TCT ACC or ATG, which hybridise with one of the above-mentioned DNA molecules under conditions which show a homology of more than 85%, preferably more than 90%, whilst these DNA molecules may be of natural, synthetic or semi-synthetic origin and may be related to these DNA molecules by mutation, nucleotide substitutions, nucleotide deletions, nucleotide insertions and inversions of nucleotides and code for polypeptides with the biological and immunological activity of EqIFN-gamma.

The invention also relates to a purified and isolated recombinant DNA molecule coding for a polypeptide which has the biological and immunological properties of EqIFN-gamma comprising the following DNA molecule, or a degenerate variant thereof:

$R^1$- TAC TGC CAG GCT GCT TTC TTT

AAA GAA ATC GAA AAC CTG AAA

GAA TAC TTC AAC GCT CGT AAC

CCA GAC GTT GGT GAC GGT GGT

CCG CTG TTC CTG GAC ATC CTG

AAA AAC TGG AAA GAA GAC TCT

GAC AAA AAG ATC ATC CAG TCT

CAG ATC GTT TCT TTC TAC TTC

AAA CTG TTC GAA AAC CTG AAA

GAC AAC CAG GTT ATC CAG AAA

-continued

TCG ATG GAC ACT ATC AAA GAA
GAT CTG TTC GTT AAA TTC TTC
AAC TCG TCG ACT TCT AAA CTG
GAA GAC TTC CAG AAA CTG ATC
CAG ATC CCA GTT AAC GAC CTG
AAA GTT CAG CGT AAG GCT ATC
TCT GAA CTG ATC AAA GTT ATG
AAC GAC CTG TCT CCA AAA GCT
AAC CTG CGT AAA CGT AAA CGT
TCT CAG AAC CCA TTC CGT GGT
CGT CGT GCT CTT CAG TAA, wherein $R^1$ represents:

ATG AAT TAT ACA AGT TTT ATC
TTG GCT TTT CAG CTG TGT GCG
ATT TTG GGT TCT TCT ACC TAT,

ATG TAT,

TAT,

ATG AAT TAT ACA AGT TTT ATC
TTG GCT TTT CAG CTG TGT GCG
ATT TTG GGT TCT TCT ACC TAC,

ATG TAC, or

TAC.

The invention also relates to a purified and isolated recombinant DNA molecule coding for a polypeptide which has the biological and immunological properties of EqIFN-gamma comprising the following DNA molecule, or a degenerate variant thereof:

$R^2$-GCT GCT TTC TTT AAA GAA ATC GAA AAC CTG AAA GAA TAC TTC
AAC GCT CGT AAC CCA GAC GTT GGT GAC GGT GGT CCG CTG TTC
CTG GAC ATC CTG AAA AAC TGG AAA GAA GAC TCT GAC AAA AAG
ATC ATC CAG TCT CAG ATC GTT TCT TTC TAC TTC AAA CTG TTC
GAA AAC CTG AAA GAC AAC CAG GTT ATC CAG AAA TCG ATG GAC
ACT ATC AAA GAA GAT CTG TTC GTT AAA TTC TTC AAC TCG TCG
ACT TCT AAA CTG GAA GAC TTC CAG AAA CTG ATC CAG ATC CCA
GTT AAC GAC CTG AAA GTT CAG CGT AAG GCT ATC TCT GAA CTG
ATC AAA GTT ATG AAC GAC CTG TCT CCA AAA GCT AAC CTG CGT
AAA CGT AAA CGT TCT CAG AAC CCA TTC CGT GGT CGT CGT GCT
CTT CAG TAA, wherein $R^2$ represents

ATG AAT TAT ACA AGT TTT ATC TTG GCT TTT CAG CTG TGT GCG ATT TTG GGT TCT

TCT ACC CAG,

ATG CAG, or

CAG.

DNA molecules:

containing the nucleotides

| | |
|---|---|
| EG-1 | 5'- TACTACTGCC AGGCTGCTTT CTTTAAAGAA ATCGAAAACC TGAAAGAATA CTTCAACGCT CG-3' |
| or | |
| EG-2 | 5'- TTGAAGTATT CTTTCAGGTT TTCGATTTCT TTAAAGAAAG CAGCCTGGCA GTAGTA-3' |
| or | |
| EG-3 | 5'- TAACCCAGAC GTTGGTGACG GTGGTCCGCT GTTCCTGGAC ATCCTGAAAA ACTGGAAAGA AGACTCTG-3' |
| or | |
| EG-4 | 5'- TTCTTTCCAG TTTTTCAGGA TGTCCAGGAA CAGCGGACCA CCGTCACCAA CGTCTGGGTT ACGAGCG-3' |
| or | |
| EG-5 | 5'- ACAAAAAGAT CATCCAGTCT CAGATCGTTT CTTTCTACTT CAAACTGTTC GAAAACCTGA AAGACAACC-3' |
| or | |
| EG-6 | 5'- TTTCAGGTTT TCGAACAGTT TGAAGTAGAA AGAAACGATC TGAGACTGGA TGATCTTTTT GTCAGAGTC-3' |
| or | |
| EG-7 | 5'- AGGTTATCCA GAAATCGATG GACACTATCA AAGAAGATCT GTTCGTTAAA TTCTTCAACT CG-3' |
| or | |
| EG-8 | 5'- TCGACGAGTT GAAGAATTTA ACGAACAGAT CTTCTTTGAT AGTGTCCATC GATTTCTGGA TAACCTGGTT GTC-3' |
| or | |
| EG-9 | 5'- TCGACTTCTA AACTGGAAGA CTTCCAGAAA CTGATCCAGA TCCCAGTTAA CGACCTGAAA-3' |
| or | |
| EG-10 | 5'- GCTGAACTTT CAGGTCGTTA ACTGGGATCT GGATCAGTTT CTGGAAGTCT TCCAGTTTAG AAG-3' |
| or | |
| EG-11 | 5'- GTTCAGCGTA AGGCTATCTC TGAACTGATC AAAGTTATGA ACGACCTGTC TCCAAAAGCT AA-3' |
| or | |
| EG-12 | 5'- CGCAGGTTAG CTTTTGGAGA CAGGTCGTTC ATAACTTTGA TCAGTTCAGA GATAGCCTTA C-3' |
| or | |
| EG-13 | 5'- CCTGCGTAAA CGTAAACGTT CTCAGAACCC ATTCCGTGGT CGTCGTGCTC TTCAGTAAG-3' |
| or | |
| EG-14 | 5'- GATCCTTACT GAAGAGCACG ACGACCACGG AATGGGTTCT GAGAACGTTT ACGTTTA-3' |
| or | |
| EG-15 | 5'- CAGGCTGCTT TCTTTAAAGA AATCGAAAAC CTGAAAGAAT ACTTCAACGC TCG-3' |
| or | |
| EG-16 | 5'- TTGAGTATT CTTTCAGGTT TTCGATTTCT TTAAAGAAAG CAGCCTG-3' |

coding for partial regions of the EqIFN-gamma and the polypeptides coded by these DNA molecules;

which hybridise with one of the above-mentioned DNA molecules under conditions which show a homology of more than 85%, preferably more than 90%, whilst the DNA molecules may be of natural, synthetic or semi-synthetic origin and may be related to these DNA molecules by mutation, nucleotide substitutions, nucleotide deletions, nucleotide insertions and inversions of nucleotides and which code for partial regions of the EqIFN-gamma, and the polypeptides coded by these DNA molecules.

Recombinant DNA molecules, for example vectors, preferably plasmids, which:

contain an insert coding for an above-mentioned polypeptide;

recombinant DNA molecules, for example vectors, preferably plasmids, which:

contain an insert coding for an above-mentioned polypeptide;

an above-mentioned DNA molecule;

an above-mentioned DNA molecule in functional connection with an expression control sequence, in microorganisms such as prokaryotes, for example *E. coli*, eukaryotes, for example *Saccharomyces cerevisiae* and mammalian cells, for example horse cells;

contain at least two of the DNA molecules designated EG-1 to EG-16 in any desired combination with one another and in functional connection with an expression control sequence, in microorganisms such as prokaryotes, for example *E. coli*, eukaryotes, for example *Saccharomyces cerevisiae* and mammalian cells, for example horse cells.

Recombinant DNA molecules such as the plasmids pAH111, pRH281/5, pRH282/5, pGN1, pGN3, pGN20, pEqG-QAA2 or pEqG-QAA3.

Host organisms transformed with one of the above-mentioned recombinant DNA molecules, for example prokaryotes, preferably *E. coli*, more particularly *E. coli* JM101 or HB101, eukaryotes, for example *Saccharomyces cerevisiae* or mammalian cell lines, preferably horse cell lines.

Processes for preparing polypeptides according to the invention, wherein a) suitable host organisms, for example those mentioned above, are transformed with genetic information coding for the polypeptides according to the invention, preferably with the above-mentioned recombinant DNA molecules, b) the information for producing the polypeptides according to the invention is expressed in the host organism and c) the polypeptides according to the invention are isolated.

Polypeptides which may be prepared by these methods.

Use of the polypeptides according to the invention for therapeutic treatment and/or for immunisation or for producing pharmaceutical preparations.

Agents for therapeutic treatment, for example of horses, characterised in that they contain in addition to pharmaceutically inert carriers an effective amount of one of the polypeptides according to the invention.

Process for preparing monoclonal antibodies against the polypeptides according to the invention, characterised in that host animals are immunised with one of the polypeptides, B-lymphocytes of these host animals are fused with myeloma cells, the hybrid cell lines secreting the monoclonal antibodies are sub-cloned and cultivated in vitro or in vivo.

Hybrid cell lines which secrete monoclonal antibodies against one of the polypeptides according to the invention.

Monoclonal antibodies which specifically neutralise, either wholly or partially, the activity of the polypeptides according to the invention or specifically bind to one of the above-mentioned polypeptides.

Use of the monoclonal antibodies for therapy and/or for the qualitative and/or quantitative determination of one of the polypeptides according to the invention.

Use of the above-mentioned monoclonal antibodies for purifying one of the polypeptides according to the invention.

Test kit for determining polypeptides according to the invention, containing the above-mentioned monoclonal antibodies.

BRIEF DESCRIPTION OF THE FIGURES

Legend relating to the drawings:

FIGS. 1*a*, 1*b*, and 1*c*: DNA sequence of the 4664 bp long BamHI fragment from lambda Eq-γ2. The encoded amino acid sequence and the position of the intron are shown. Amino acids with a negative number indicate the hydrophobic signal peptide. The only potential N-glycosylation site of the mature EqIFN-γ at position 86–88 is underlined. The sequences CCATC and TATAAAA important for the binding of the RNA polymerase are underlined, as are two signal sequences for the polyadenylation of mRNA (AATAAA).

FIG. 2: Comparison of the amino acid sequences of gamma-interferons of different species. The amino acids whose numbers are preceded by "S" indicate the signal peptide. The "consensus" sequence shows, in capital letters, those amino acids which are identical in all the gamma-interferons, whilst the small letters indicate the amino acids which occur in more than 75% of gamma-interferons.

FIGS. 3A and 3B: Schematic representation of the oligonucleotides used for total synthesis of the horse gamma-interferon gene. The length of the individual oligonucleotides and their numbering are given. Restriction cutting sites which occur only once within the synthetic gene are numbered.

FIGS. 4A and 4B: Comparison of the coding sequences for mature EqIFN-γ of the natural gene (eq) and the synthetic gene (syn) optimally designed for expression in *E. coli.* Differing bases are marked with an asterisk.

FIG. 5: Table showing the codons used for mature EqIFN-γ. The first base is shown at the left-hand edge, the second base in the centre and the third base of the codon at the right-hand edge. The table shows the number of codons used for the amino acid in question in the natural gene whilst those of the synthetic gene are shown in brackets.

EXAMPLES

Figure 6:
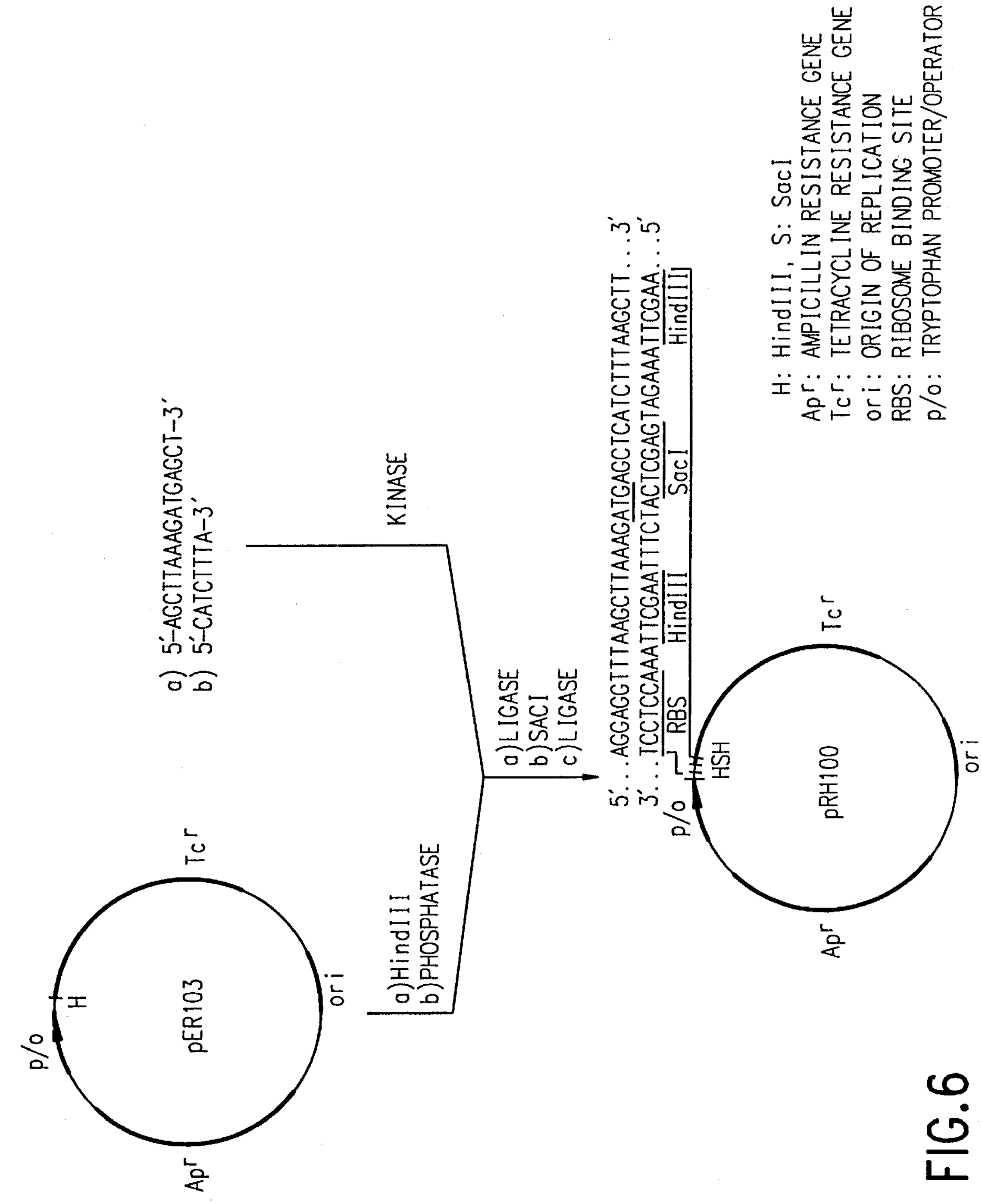
FIG. 6: Construction of the expression plasmid pRH100.
Figure 7A:
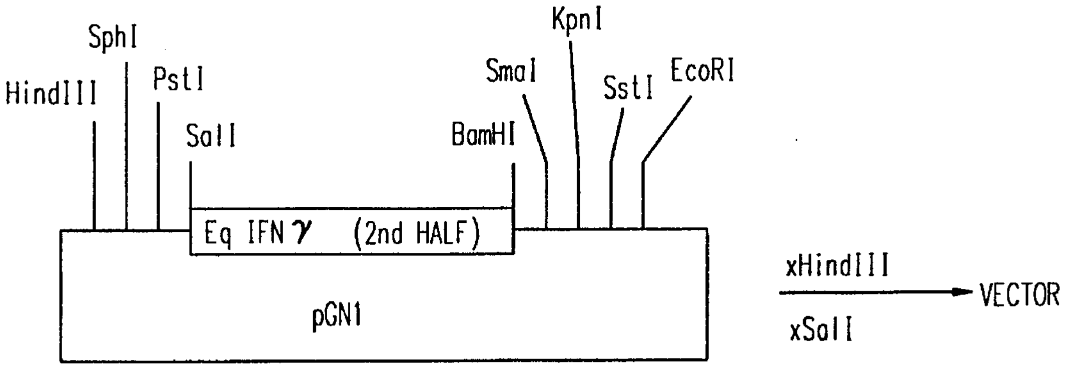
FIGS. 7A, 7B and 7C: Construction and restriction map of pGN20.
Figure 7B:
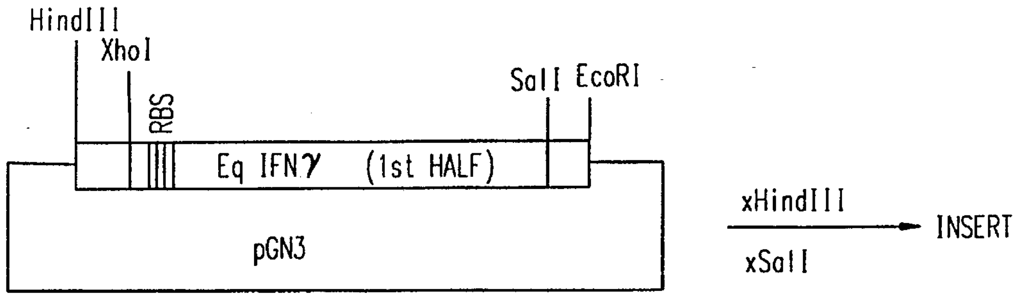
Figure 7C:
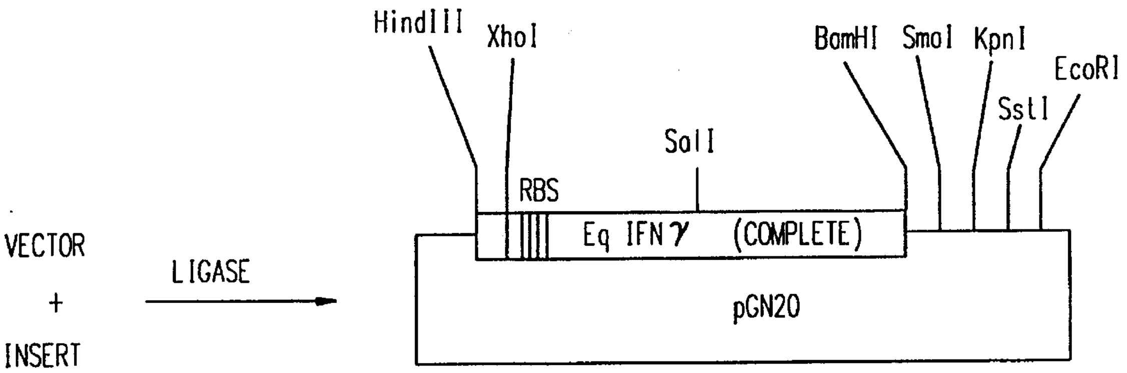

The Examples which follow, which should not restrict the invention, describe it in detail.

Materials

The starting materials are obtained commercially in some cases and in other cases they originate from EMBL in Heidelberg. *E. coli* JM101, pUC9 and M13mp8 came from the Bethesda Research Laboratories, the *E. coli* strains with the suppressor factor sup F, for example *E. coli* NM526, 538 and 539 and the vector lambda EMBL3 or 3A came from EMBL and are also obtainable from the company Stehelin/Basle (Switzerland).

1. Isolation of horse DNA

Frozen tissue, e.g. horse liver, was ground to a powder in liquid nitrogen and incubated for 3 hours at 55° C. in 0.5M EDTA, 10 mM Tris-HCl pH 8.0, 0.5% SDS and 0.1 mg/ml of proteinase K (20 ml/g of tissue). The viscous solution obtained is freed from protein by phenol extraction and extracting three times with phenol/chloroform/isoamyl alcohol (25/24/1 vol), dialysed against 50 mM Tris-HCl pH 8.0, 10 mM EDTA and 10 mM NaCl and the DNA was precipitated with 2 volumes of ethanol. After being dried completely in vacuo, the DNA was put into solution in TE buffer (10 mM Tris-HCl pH 8.0, 1 mM EDTA) at 4° C. and centrifuged with 1.273 g of CsCl/ml solution for 62 hours at 40,000 rpm and at 20° C. (Sorvall 50Ti rotor). The CsCl gradient was allowed to drip out, the fractions containing DNA were dialysed against TE buffer and the DNA was then precipitated with 2 volumes of ethanol, washed with 70% ethanol, dried and redissolved in TE buffer (4° C.).

The final DNA preparation was free from RNA and longer than 50 kb (determined by electrophoresis on a 0.45% agarose gel).

2. Partial endonuclease digestion and size fractionation of horse DNA

Twice 50 mcg of horse DNA were incubated with 1.6 units of Sau3A in 450 mcl of reaction medium (10 mM Tris-HCl pH 7.5, 10 mM $MgCl_2$, 1 mM dithiothreitol) at 37° C. After 15, 25 and 40 minutes, 150 mcl aliquots were taken and mixed with 15 mM EDTA. After 10 minutes heating to 70° C. the reaction was stopped. After the addition of 0.3M Na acetate, pH 6.0, the DNA was precipitated with 2.5 volumes of ethanol. After re-dissolving in TE buffer, the DNA was separated electrophoretically overnight according to size on a 0.45% agarose gel in TBE buffer (10.8 g/l Tris, 5.5 g/l boric acid, 0.93 g/l $Na_2EDTA$) at about 1 V/cm. Using size markers (lambda-DNA doubly digested with EcoRI and HindIII and digested with HindIII) the gel fragment with DNA 10–23 kb long was cut out, the DNA was electroeluted from the gel in a dialysis tube for 3 hours at 300 V (buffer 0.1×x TBE), purified on an Elutip-D column (Schleicher and Schell) according to the manufacturer's instructions for use and subsequently precipitated with ethanol.

In order to prevent the self-ligation of horse DNA fragments, which might result on the one hand in artificial hybrids of horse DNA sequences and on the other hand in excessively large DNA fragments which can therefore not be packaged in lambda phages, the size-fractionated horse DNA fragments were dephosphorylated. To do this, the DNA is incubated in 140 mcl of reaction medium (50 mM Tris-HCl pH 9.5, 10 mM $MgCl_2$, 0.1 mM Zn acetate, 1 mM spermidine) with 5 units of bovine intestinal phosphatase for 30 minutes at 37° C., a further 5 units of enzyme were added and the resulting mixture was incubated for 30 minutes. After the addition of EDTA to give a final concentration of 25 mM, the DNA was extracted once with phenol/chloroform/isoamyl alcohol (25/24/1 vol), twice with chloroform/isoamyl alcohol (24/1 vol) and three times with diethylether, precipitated with ethanol, dried and dissolved in 0.1×TE buffer.

3. Constructing the horse genome DNA library

The dephosphorylated 10–23 kb horse DNA fragments were cloned in a lambda vector, for example lambda-EMBL3 or 3A (Frischauf, A. M. et al. J. Mol. Biol., 170,827–842 (1983)) with G-A-T-C cohesive ends, obtained by removing the internal BamHI fragment of the phage DNA.

The vector was grown in an *E. coli* strain with suppressor factor sup F, for example *E. coli* NM526, 538 or 539 (Frischauf, A. M. et al. J. Mol. Biol., 170, 827–842 (1983)), in LB broth (Miller; Experiments in Molecular Genetics; Cold Spring Harbor Lab., Cold Spring Harbor, N.Y.) with 5 mM $MgSO_4$, precipitated with polyethylene glycol and purified by centrifuging twice on a CsCl density gradient (0.71 g CsCl/ ml of solution, 40 hours at 45,000 rpm, 20° C.) . After dialysis against TE buffer, the phage DNA was freed from protein by extraction twice with phenol/chloroform/isoamyl alcohol (25/24/1 vol) and extraction twice with chloroform/isoamyl alcohol (24/1 vol) and concentrated by ethanol precipitation.

In order to obtain the end fragments of EMBL3A, 50 mcg of phage DNA were totally digested with BamHI for 2 hours at 37° C. in 450 mcl of reaction medium (10 mM Tris-HCl pH 7.5, 10 mM $MgCl_2$, 1 mM dithiothreitol), the reaction was stopped with 15 mM EDTA at 70° C. for 10 minutes and the DNA was precipitated with ethanol.

In order to prevent religation the centre fragment was re-cut with EcoRI and the oligonucleotide which fell away was removed by isopropanol precipitation.

The BamHI-digested lambda DNA was totally digested with EcoRI for 2 hours at 37° C. in 450 mcl of 10 mM Tris-HCl pH 7.5, 100 mM NaCl and 10 mM $MgCl_2$ and the reaction was stopped by the addition of 15 mM EDTA and heating for 10 minutes to 70° C. After the addition of Na acetate to give a final concentration of 0.3M, the 3 large DNA fragments were precipitated with 0.6 volumes of isopropanol for 15 minutes at 0° C., washed twice with 0.45M Na acetate/0.6 volumes isopropanol and once with 0.3M Na acetate/2.5 volumes of ethanol and dissolved in 15 mcl of 0.1×TE buffer. The BamHI/EcoRI linkers remain in solution during this procedure. The EMBL3A fragments (8 mcg) were combined with about 5 mcg of 10–23 kb horse DNA and 10 units of T4-DNA ligase (NEN) and incubated overnight at 14° C. and for one day at 4° C. in 50 mcl of ligation medium (66 mM Tris-HCl pH 7.2, 0.1M NaCl, 10 mM $MgCl_2$, 1 mM EDTA, 5 mM dithiothreitol, 0.5 mM ATP). The ligated DNA mixture was packed into mature lambda phage particles using an in vitro lambda packaging system (Scalenghe, F. et al; Chromosoma, 82, 205–216 (1981)).

The components of this system, namely ultrasound extract (SE), freeze-thaw lysate (FTL), buffer M1 and A were prepared in accordance with Scalenghe, F. et al; Chromosoma, 82, 205–216 (1981). 10 mcl aliquots of the ligated DNA mixture were incubated for 2 minutes at ambient temperature with 25 mcl of SE which, like FTL, had been thawed out from ice for 30 minutes, mixed with 100 mcl of FTL and re-incubated for 60 minutes at ambient temperature. The packing mixture was diluted with 150 mcl of lambda diluent (100 mM Tris-HCl pH 7.5, 10 mM $MgSO_4$, 1 mM EDTA) and stored at 4° C.

4. Cloning and sequencing of the gene for horse gamma-interferon (EqIFN-γ)

A. Isolation of a complete EqIFN-γ gene clone

The equine DNA library was used to infect the *E. coli* strain NM528 (supF). A bacterial culture which had been grown overnight in LB nutrient solution (10 g/l tryptone, 5 g/l yeast extract, 10 g/l NaCl, pH 7.4) with 0.2% maltose was adjusted to an optical density (600 nm) of 2.0 in 10 mM $MgSO_4$. 0.5 ml batches of this suspension were infected with 50,000 pfu (plaque forming units) of lambda phage from the DNA library and using a soft LB agar layer, distributed on LB agar plates with 10 mM $MgSO_4$ (13.5 cm diameter). In all, $1.5\times10^6$ recombinant lambda phage were screened. After incubating overnight at 37° C. two replicas were prepared on nitrocellulose from the phage on each plate (Benton and Davis, Science 196:180–182, 1977). After denaturation of the phage DNA (1 min in 0.5N NaOH, 1.5M NaCl), neutralising (twice 3 minutes in 0.5M Tris-HCl pH 7.5, 1.5M NaCl) and rinsing (1 min in 2×SSC, 1×SSC, 0.15M NaCl, 15 mM Na citrate) the filters were dried in air and the DNA was fixed by baking for 2 hours at 80° C. The filters were washed overnight at 65° C. in a solution of 1.5M NaCl, 10 mM Tris-HCl, pH 8.0, 0.1% SDS and pre-hybridised for 4 to 6 hours at 65° C. (hybridising solution: 0.9M NaCl, 50 mM $NaH_2PO_4$, pH 7.4, 5 mM EDTA, 0.1% FiColl, 0.1% polyvinylpyrrolidone, 0.1% bovine serum albumin, 0.1% SDS, 20 mg/ml of sonicated and denatured salmon sperm DNA). Hybridisation was carried out in a fresh solution with $10^6$ cpm per filter of a HuIFN-γ probe radioactively labelled by conventional methods and lasted for 20 hours at 65° C. The filters were washed under non-stringent conditions in 3×SSC, 0.1% SDS at 65° C., dried and autoradiographed. After three plaque purification treatments 5 lambda clones were identified which gave positive hybridisation signals.

From these isolated recombinant phage the DNA was purified by conventional methods (Maniatis et al., ibid.). The phage DNAs were characterised by digestion with various restriction enzymes and subsequent Southern analysis after hybridisation with the HuIFN-γ probe (Southern, J. Mol. Biol. 98: 503–517, 1975). A single hybridising 4.6 kb long BamHI fragment of the clone lambda Eq-γ2 was isolated and cloned into the BamHI cutting site of the plasmid pUC9 (Vieira and Messing, Gene 19: 259–268, 1982). After transformation of *E. coli* JM101, plasmid DNA was prepared from the colonies obtained by a mini-preparation process (Birnboim and Doly, Nucl. Acids Res. 7: 1513–1523, 1979) and characterised by digestion with restriction enzymes. A plasmid with the desired BamHI insert was designated pAH111. The ends of the BamHI insert of plasmid pAH111 were sequenced by the dideoxy method (Sanger et al., Proc. Natl. Acad. Sci. USA 74: 5463–5467, 1977) after introduction into the M13mp8 and M13mp9 vectors (Vieira and Messing, Gene 19, 259–268, 1982). A sequence comparison with the human gamma-interferon gene (Gray and Goeddel, Nature 298: 859–863, 1982) showed a high degree of homology with the non-coding 5' and 3' regions. It was concluded from this that the complete EqIFN-γ gene had been isolated.

B. Sequencing of the horse gamma-interferon gene from clone lambda Eq-γ2.

The 4.6 kb long BamHI insert of plasmid pAH111 was sequenced completely using the dideoxy method. The total sequence of the BamHI fragment was determined by combining partial sequences of M13 subclones which had been obtained by direct cloning of restriction fragments (EcoRI, HindIII, PstI, PstI-BglII, HindIII-BamHI) into correspondingly cut M13mp8 or M13mp9 vectors. Other partial sequences were obtained by cloning the 2.0 kb long BamHI-BglII fragment, or the 2.0 kb long PstI fragment, into the M13mp8 vector by the "shotgun" method. The two DNA fragments were divided into smaller pieces by ultrasound and the ends of the DNA were blunted by incubation with *E. coli* DNA polymerase I (Klenow fragment) in the presence of 0.1 mM of each of the four deoxynucleotide triphosphates (reaction buffer: 50 mM Tris-HCl pH 7.5, 10 mM $MgCl_2$, 1 mM dithiothreitol, 0.5 mg/ml bovine serum albumin: 1 hour at 25° C.). After size fractionation in an agarose gel, DNA fragments with a length of about 0.4 to 1.0 kb were isolated and ligated into the SmaI cutting site of the M13mp8 vector. The partial sequences obtained were combined by means of a computer program to give the total sequence 4664 bp long which is shown in FIGS. 1*a*–1*c*.

By computer-aided analysis of the open reading frame and comparison with gamma-interferon genes of other species (Gray and Goeddel, Nature 298; 859–863; Gray and Goeddel, Proc. Natl. Acad. Sci. USA 80: 5842–5846, 1983; Dijkema et al., EMBO J. 4: 761–767, 1985; Cerretti et al., J. Immunology 136: 4561–4564, 1986) the protein-coding region of the equine gamma-interferon gene was determined. The protein coding region is interrupted by three introns, the first exon encoding the hydrophobic signal peptide which is 20 amino acids long and 18 amino acids of the mature EqIFN-γ polypeptide (bases 366–479). The second exon codes for the amino acids 19–41 (bases 1639–1707), the third exon codes for the amino acids 42–102 (bases 1803–1985), the fourth exon encodes the carboxy terminus with amino acids 103–146 (bases 3307–3441). At positions 4010 and 4020 there are two signal sequences (AATAAA) for the polyadenylation of mRNA. At positions 86–88 of the mature EqIFN-γ polypeptide is the single potential N-glycosylation site (ASN-Ser-Ser) which coincides with the second N-glycosylation site of bovine gamma-interferon (Asn-Gly-Ser) (FIG. 2). Surprisingly, the mature EqIFN-γ polypeptide contains only a single cysteine group at position 3, whilst analogously to the natural human and murine gamma interferons the first three amino-terminal amino acids (in this case Tyr-Tyr-Cys) are probably cleaved proteolytically in the organism.

5. Preparation of a synthetic gene for mature EqIFN-γ

In order to express recombinant EqIFN-γ in its mature form in *Escherichia coli*, a synthetic gene was constructed from oligonucleotides. It codes for the same amino acid sequence as the natural EqIFN-γ gene but contains only those codons for the individual amino acids which are used in native cell genes highly expressed by *E. coli* (Gouy and Gautier, Nucl. Acids Res. 10: 7055–7074, 1982). In addition, several single restriction enzyme cutting sites were incorporated which make it easy to manipulate the gene in order to change individual sections. The synthetic gene for EqIFN-γ was constructed in two alternative forms from a total of 16 different oligonucleotides. The first variant codes for mature EqIFN-γ with 146 amino acids plus start methionine, whilst the second form codes for a polypeptide shortened by 3 amino acids (Tyr-Tyr-Cys) at the amino terminus plus start methionine, as would presumably occur in the natural organism.

The structure of the synthetic EqIFN-γ gene is shown in FIGS. 3A and 3B. The oligonucleotides used for its preparation were synthesised using an Applied Biosystems Model 381A DNA Synthesiser, purified by electrophoresis in denaturing 12% polyacrylamide gels (7M urea) and desalinated by exclusion chromatography on Sephadex G-25 (Pharmacia).

Combining the oligonucleotides to produce the synthetic EqIFN-γ gene

The synthetic EqIFN-γ gene was produced in two parts. The first part of the gene, up to the SalI cutting site, was produced using the eight oligonucleotides EG-1 to EG-8 whilst the second half of the gene, from the SalI cutting site to the BamHI cutting site, was prepared from the six oligonucleotides EG-9 to EG-14. For the form of EqIFN-γ shortened by three amino acids at the amino terminus, the oligonucleotides EG-15 and EG-16 were used instead of the oligonucleotides EG-1 and EG-2.

The oligonucleotides complementary to each other were phosphorylated in pairs at the 5' end. 100 pMol of the two oligonucleotides (for example EG-3 and EG-4, or EG-5 and EG-6, etc.) were incubated in 9 mcl of kinase buffer (70 mM Tris-HCl pH 7.6, 10 mM $MgCl_2$, 5 mM dithiothreitol), 2 mcCi [$\gamma^{32}P$]ATP (Amersham) with 10 units of T4-polynucleotide kinase (New England Biolabs) for 10 minutes at 37° C. Then 1 mcl of a 10 mM ATP solution was added and the mixture was incubated at 37° C. for a further 50 minutes. The reaction was stopped by heating to 95° C. for 10 minutes. To prevent subsequent ligation of the DNA ends, the oligonucleotides EG-1, EG-15, EG-9 and EG-14 were not phosphorylated. After deactivation of the polynucleotide kinase, they were mixed with the complementary oligonucleotide, heated to 95° C. for 5 minutes and cooled to ambient temperature.

The mixtures of the oligonucleotides EG-1+2 (or in a second batch EG-15+16), EG-3+4, EG-5+6 and EG-7+8 were combined, mixed with 1 mcl of 5M NaCl, heated to 70° C. for 5 minutes and cooled to ambient temperature. 5 mcl of 10 mM ATP, 2 mcl of dithiothreitol, 1.5 mcl of 10×ligation buffer (0.66M Tris-HCl pH 7.2, 1M NaCl, 100 mM $MgCl_2$, 10 mM EDTA, 50 mM dithiothreitol) and 80 units of T4 DNA ligase (New England Biolabs) were added to this solution which was then incubated at 4° C. for 48 hours. The course of the ligase reaction was monitored by gel-electrophoretic separation of the DNA fragments from a small part of the reaction in a 5% non-denaturing polyacrylamide gel and subsequent autoradiography.

In the same way, the six oligonucleotides EG-9 to EG-14 were linked together. The reaction was stopped by extraction with phenol/chloroform and the DNA was recovered by ethanol precipitation.

6. Construction of the expression plasmid pRH 100

All the enzyme reactions were carried out under the conditions specified by the manufacturers.

7 mcg of plasmid pER103 (Eva Dworking-Rastl et al., Gene 21 (1983), 237–248: EP-A-0155613) were linearised in 50 mcl of reaction medium with the restriction endonuclease HindIII. After one hours incubation at 37° C. 50 mcl of 2×CIP buffer were added (2×CIP buffer=20 mM Tris, pH=9.2, 0.2 mM EDTA). By adding 2 units of calf intestinal alkaline phosphatase (CIP) the 5' terminal phosphate residues were eliminated; incubation was carried out at 45° C. for 30 minutes. The reaction was stopped by the addition of 4 mcl of 0.5M EDTA solution and by adding 10 mcl of 1M Tris, pH=8.0 solution. The proteins were removed by extracting twice with phenol and once with phenol/chloroform. The DNA was precipitated from the aqueous phase after the addition of 0.1 vol of 3M sodium acetate solution pH 5.5 and 250 mcl of ethanol, the DNA precipitate was centrifuged and washed once with 70% ethanol solution. The DNA was dried and the pellet was dissolved in 20 mcl of TE buffer (10 mM Tris pH 8.0, 1 mM EDTA).

1 mcg batches of the synthetically prepared oligonucleotides d(AGCTTAAAGATGAGCT) and d(CATCTTTA) were phosphorylated in 10 mcl of reaction solution with the addition of 10 units of T4-PNK (polynucleotide kinase) and 1 mM rATP. The reaction took place at 37° C. and lasted 45 minutes. It was stopped by heating to 70° C. for 10 minutes.

5 mcl batches of the plasmid solution and the phosphorylated oligonucleotides were mixed together and heated to 70° C. for 5 minutes. Then the solution was cooled to 0° C., 2 mcl of 10×ligase buffer (500 mM Tris, pH=7.5, 100 mM $MgCl_2$, 200 mM DTT (dithiothreitol), 1 mM rATP, 500 mcg/ml BSA (bovine serum albumin)), 2 mcl of water and 10 units of T4-DNA ligase were added. The reaction lasted 40 hours and was carried out at 4° C. It was stopped by heating to 70° C. for 10 minutes.

2 mcl of this ligase reaction were digested with 10 units of the restriction endonuclease SacI (New England Biolabs) for 3 hours at 37° C. in a total of 30 mcl of solution. The reaction was stopped by heating to 70° C. for 10 minutes. 5 mcl of this reaction mixture were ligated in a total of 30 mcl by the addition of 10 units of T4-PNK at 14° C. for 16 hours.

200 mcl of competent *E. coli* HB101 were combined with 10 mcl of this ligase reaction. The bacteria were kept on ice for 45 minutes and then heated to 42° C. for 2 minutes in order to allow the uptake of DNA. The bacterial suspension was then incubated again at 0° C. for 10 minutes. Finally, the transformed bacteria were spread on an LB agar containing 50 mcg/ml of ampicillin.

Of the bacterial colonies formed, 12 were chosen at random and the plasmids were isolated from them on a small scale (Birnboim and Doly, Nucl. Acids Res. 7 (1979), 1513–1523). The resulting DNA was cut with the restriction endonuclease SacI and the DNA was resolved on an agarose gel (1%, 1×TBE buffer). The migration of the DNA as a linear molecule about 4400 bp long confirmed that a SacI recognition site had been inserted into the plasmid. One of these plasmids was selected at random. Once again, *E. coli* HB101 was transformed with the DNA from the associated mini-preparations. Of the resulting transformed bacteria, one colony was selected and cultivated on a larger scale. The plasmid isolated therefrom was cut with the restriction endonucleases EcoRI and BamHI, the DNA was resolved on a 1% agarose gel and the smaller fragment was isolated from the gel by electroelution. This EcoRI-BamHI DNA fragment about 460 bp long was sequenced according to Sanger (F. Sanger, et al, Proc. Natl. Acad. Sci. (1977), 5463–5467). The plasmid thus analysed was designated pRH100.

7. Insertion of the synthetic EqIFN-γ gene into the expression plasmid pRH100

10 mcg of plasmid pRH100 are totally cut with SacI in 100 mcl of reaction buffer and the enzyme is inactivated by heating to 70° C. for 10 minutes. The overhanging DNA ends are straightened by treating with Klenow fragment (Amersham) in the presence of 10 mcM of each of the four deoxynucleotide triphosphates (30 min., 25° C.). The reaction is stopped by extraction with phenol/chloroform and the DNA is concentrated by ethanol precipitation. This treatment produces, adjoining the tryptophan promoter, a blunt DNA end which ends with the translation start codon "ATG". The linearised plasmid DNA is re-cut with BamHI and the vector portion is isolated after electrophoretic separation from an agarose gel.

50 ng of the pRH100 plasmid vector prepared as described are mixed with 20 pmol of the ligated oligonucleotides EG-1 to EG-8 and EG-9 to EG-14 and incubated in 10 mcl of ligation buffer (66 mM Tris-HCl pH 7.2, 100 mM NaCl, 10 mM $MgCl_2$, 1 mM EDTA, 5 mM dithiothreitol, 1 mM ATP) with one unit of T4 DNA ligase (Boehringer Mannheim) for 24 hours at 14° C. *E. coli* JM101 made competent by treatment with calcium chloride is transformed with this ligation mixture and incubated overnight at 37° C. From the transformants obtained, plasmid DNA is isolated by the mini-preparation method and the structure is determined by restriction analysis and sequencing of the HindIII-BamHI insert. A plasmid of the desired structure for the expression of mature EqIFN-γ is designated pEqG-YYC1. Completely analogously, the oligonucleotides EG-15, EG-16, EG-3 to EG-8 and EG-9 to EG-14 are cloned into the pRH100 vector in order to obtain EqIFN-γ which is shortened by three amino acids. A plasmid of the desired structure is designated pEqG-QAA1.

8. Expression of the interferon activity by *E.coli* JM101 containing the plasmid pEq-YYC1 or pEqG-QAA1

100 ml of bacterial culture are incubated at 37° C., with vigorous shaking, in the following tryptophan-free medium (amounts given per liter of medium): 10 g $(NH_4)_2PO_4$, 3.5 g $KH_2PO_4$ pH 7.3 with NaOH, 0.5 g NaCl, 21 g casamino acids (acid-hydrolysed), 11 g glucose, 1 mM $MgSO_4$, 0.1 mM $CaCl_2$, 1 mg thiamine-HCl, 20 mg L-cysteine, 20 mg 3-β-indolacrylic acid (IAA, inducer of the tryptophan-operon), and optionally 50–100 mg of ampicillin. The bacteria are then pelleted by centrifuging for 5 minutes at 4000 rpm, suspended with 1/10 of the culture volume of ice cold 50 mM Tris-HCl, pH 8.0, 30 mM NaCl and broken up by use of an ultrasonic probe (20 kHz, 100 Watt) twice for 30 seconds whilst cooling with ice. The cell debris is removed by centrifuging for 10 minutes at 10,000 rpm (4° C.) and after being sterile filtered the supernatant is tested for interferon activity in an assay which measures the cytopathic effect (CPE) of vesicular stomatitis virus (VSV) or encephalomyocarditis virus (EMCV).

Test system:

NBL-6 cells (ATCC CCL 57, horse hide epidermis cells)/VSV A549 (ATCC CCL 185, human lung cancer cell line)/EMCV.

The titre of A549 cells is standardised to international units using human interferon standard.

Detection of the expressed horse interferons by labelling the proteins in maxicells Plasmid-coded proteins can be labelled selectively in vivo using the maxicell technique. *E. coli* CSR603 is transformed with the expression plasmids in the usual way and selected from transformed bacteria on agar plates containing ampicillin. The preparation of the maxicells and the labelling of the proteins are carried out as prescribed by A. Sancar (loc.cit.). The cells are cultivated in 15 ml of medium (see Example 8) without indoleacrylic acid at 37° C. up to an $OD_{600nm}$=0.5 and 10 ml of this culture are irradiated in a Petri dish for 5 seconds at a distance of 50 cm using a UV germicidal lamp (15 Watts), whilst being pivoted, and incubated for a further hour at 37° C. The cultures are mixed with 100 mcg/ml of D-cycloserine, incubated for 14 hours at 37° C. and the bacteria are then harvested by centrifuging. The cells are washed twice with 5 ml of Hershey salt solution, suspended in 5 ml of Hershey medium with 20 mcg/ml of indoleacrylic acid and incubated for 2 hours at 37° C. 5 mcCi/ml of $^{35}$S-methionine (1000 Ci/mMol) were added to each culture which was then shaken for 1 hour at 37° C. The cells were harvested, lysed in electrophoresis probe buffer containing SDS and 2-mercaptoethanol and the proteins were separated on a 15% polyacrylamide gel.

| Hershey saline solution (per liter) | Hershey medium (per 100 ml of Hershey saline solution) | |
|---|---|---|
| 5.4 g NaCl | 2 ml | 20% glucose |
| 3.0 g KCl | 0.5 ml | 2% threonine |
| 1.1 g $NH_4Cl$ | 1.0 ml | 1% leucine |
| 15 mg $CaCl_2.2H_2O$ | 1.0 ml | 2% proline |
| 0.2 g $MgCl_2.6H_2O$ | 1.0 ml | 2% arginine |
| 0.2 mg $FeCl_3.6H_2O$ | 0.1 ml | 0.1% thiamine |
| 87 mg $KH_2PO_4$ | | |
| 12.1 g Tris-HCl pH 7.4 | | |

An autoradiogram of the dried gel is prepared after 2 days' exposure on DuPont Cronex X-ray film using a Kodak Lanex-Regular Intensifier film at −80° C. A $^{14}$C-methylated protein mixture (Amersham) is used as the molecular weight standard. The controls used are the plasmid pER103, which contains only the promoter but no interferon gene, and the plasmid pER21/1, which contains two copies of the human IFN-α2arg gene.

10. Detection of sequences in genomic horse DNA hybridising with EqIFN-γ

The following procedure is used to detect the total number of sequences in the horse genome which show a high degree of homology with the interferon gene EqIFN-γ. 30 mcg of high molecular horse DNA (Example 1) are totally digested with 100 units of the corresponding restriction enzyme in 300 mcl reaction volume and 10 mcg of this cut DNA is resolved according to size in each track on a 0.8% agarose gel.

After Southern transfer onto nitrocellulose filters, denaturing and fixing the DNA, each filter is hybridised with about $6\times10^6$ cpm of radioactively labelled "probe" (17 hours at 65° C. 5×SSC 5×Denhardt solution, 0 1% SDS, 20 mcg/ml of denatured salmon sperm DNA). The probe used for EqIFN-γ is a fragment of the plasmid pEqG-YYC1 which contains the coding sequence for the entire mature interferon. The filters are then washed under stringent conditions: 4 times, 45 minutes at 65° C. with 0.3×SSC (45 mM NaCl, 4.5 mM $Na_3$ citrate), 0.1% SDS. Autoradiography is effected on DuPont Cronex X-ray film using Kodak Lanex-Regular Intensifier film over a period of 7 days at −80° C.

11. Expression of equine interferon-gamma (QAA) in *E. coli* HB101/pEqG-QAA2 and HB101/pEqG-QAA3

In order to achieve better expression a) improved expression vectors and b) an improved ribosomal binding site were used. The improved expression vectors are based on the trp promoter from *Serratia marcescens* (S.ma) in which the -35 region is adjusted to the consensus -35 region by a base exchange (pRH281), or on a hybrid trp promoter which possesses the first A/T-rich region of *Escherichia coli* (E.co) or the second A/T-rich region plus promoter of S.ma (pRH282, S. Itoh, Gene 44 (1966) , 29–36). The ribosomal binding site used was that of *E. coli* enterotoxin II.

a) pRH281/5

The following oligonucleotides were prepared using an Applied Biosystems DNA Synthesiser 381A:

Trp-1: 5'-AATTGACGCTG-3'

Trp-3: 5'-ATCGCTAAAACATTGTGCAAAAAGAGGGTTGACATTGCCTTCGCGAACCA
GTTAACTAGTACACA-3'

Trp-5: 5'-AGTTCACGGCTCGAGACGGTAAGGAGGTTTAATATGAGCTCGAATTCAT-3'

Trp-2: 5'-TTAGCGATCAGCGTC-3'

Trp-4: 5'-CGTGAACTTGTGTACTAGTTAACTGGTTCGCGAAGGCAATGTCAACCCT
CTTTTTGCACAATGTT-3'

Trp-6: 5'-CGATGAATTCGAGCTCATATTAAACCTCCTTACCGTCTCGAGC-3'

100 pMol of oligonucleotides Trp-2 to Trp-5 were phosphorylated separately in 10 mcl. Trp-1 and -2, Trp-3 and -4 and Trp-5 and -6 were hybridised by boiling and slow cooling. The solutions of the oligonucleotide pairs were combined and ligated by the addition of T4-DNA ligase. 3 mcg of pAT153 were doubly cut with EcoRI and ClaI. After the large fragment had been purified it was combined with about 20 pMol of oligonucleotides and ligated. The DNA was subsequently transformed into *E. coli* HB101 and the plasmids from some resulting colonies were isolated. The Pst-HindIII fragment containing the promoter was sequenced. After the desired sequence had been confirmed a plasmid was selected and designated pRH281/5.

The sequence of the promoter part reads as follows:

```
                                                    −35
5'-GAATTGACGCTGATCGCTAAAACATTGTGCAAAAAGAGGGTTGACATTGC
3'-CTTAACTGCGACTAGCGATTTTGTAACACGTTTTTCTCCCAACTGTAACG

                                        XhoI
              −10            !Transkriptionsstart
CTTCGCGAACCAGTTAACTAGTACACAAGTTCACGGCTCGAGACGGTAAG
GAAGCGCTTGGTCAATTGATCATGTGTTCAAGTGCCGAGCTCTGCCATTC

RBS         SstI   EcoRI   ClaI
GAGGTTTAATATGAGCTCGAATTCATCGAT-3'
CTCCAAATTATACTCGAGCTTAAGTAGGTA-5'
```

The advantages of the new expression vector are:

1) optimal-35 region in the trp-S.ma promoter
2) single XhoI site in front of the ribosomal binding site (RBS) permits the exchange of the RBS for another
3) the expression plasmid contains a translation start ATG at a spacing of 5 nucleotides after the RBS
4) the G of this ATG is the first base of the SstI recognition sequence (GAGCTC). By cutting with SstI and subsequently producing a straight end, an expression vector with a translation start ATG is provided, into which a foreign gene can be ligated starting with the first base of the reading frame.
5) the connection RBS-ATG contains no G or C
6) by the choice of the oligonucleotide sequence at the 5' end the original EcoRI cutting site was destroyed. As a result, a multi-cloning site consisting of SstI, EcoRI, ClaI and HindIII (already in the pAT153 part) may be produced at the 3' end of the promoter.

b) pRH282/5

The expression vector pRH282/5 was built up in the same way. The oligonucleotides Trp-1 and Trp-2 were replaced by the oligonucleotides Trp-7 and Trp-8:

```
Trp-7: 5'-AATTGCCCGTTCTGGATAATGTTTTTTGCGCCGACATCATCATGCT-3'

Trp-8: 5'-TTAGCGATCAGCATGATGATGTCGGCGCAAAAAACATTATCCAGAACGGGC-3'
```

The sequence of the promoter part in DRH282/5 reads as follows:

```
5'-GAATTGCCCGTTCTGGATAATGTTTTTTGCGCCGACATCATCATGCTGAT
3'-CTTAACGGGCAAGACCTATTACAAAAAACGCGGCTGTAGTAGTACGACTA

                                  −35
CGCTAAAACATTGTGCAAAAAGAGGGTTGACATTGCCTTCGCGAACCAGT
GCGATTTTGTAACACGTTTTTCTCCCAACTGTAACGGAAGCGCTTGGTCA

                        XhoI
−10          !Transkriptionsstart            RBS
TAACTAGTACACAAGTTCACGGCTCGAGACGGTAAGGAGGTTTAATATGA
ATTGATCATGTGTTCAAGTGCCGAGCTCTGCCATTCCTCCAAATTATACT

SstI   EcoRI   ClaI
GCTCGAATTCATCGAT-3'
CGAGCTTAAGTAGCTA-5'
```

c) pGN1

1 mcg of pUC18 was doubly cut with BamHI and SalI. From 10 mcg of EqG-QAA1, again by doubly cutting with BamHI-SalI, the second half of the synthetic horse gamma-interferon gene was isolated and dephos phorylated. About 20 ng of vector were ligated with 100 ng of insert and the DNA was transformed into *E. coli* JM101. The plasmid of one colony was tested by restriction enzyme digestion and designated pGN1.

d) pGN3

The first half of the synthetic gene was made up of oligonucleotides, together with the ribosomal binding site:

EqG-1: 5'-AGCTTCCCTCGAGAGGTTGAGGTGATTTATGCAGGCTGCTTTCTTTAAAG
AAATCGAAAACCTGAAAGAATACTTCAACGCTCGTAACCCAGACGTTGGT-3'

EqG-2: 5'-GACGGTGGTCCGCTGTTCCTGGACATCCTGAAAAACTGGAAAGAAGACTC
TGACAAAAAGATCATCCAGTCTCAG-3'

EqG-3: 5'-ATCGTTTCTTTCTACTTCAAACTGTTCGAAAACCTGAAAGACAACCAGGT
TATCCAGAAATCGATGGACACTATCAAAGAAGATCTGTTCGTTAAATTCT
TCAACTCGTCGACTCCG-3'

EqG-4: 5'-AATTCGGAGTCGACGAGTTGAAGAATTTAACGAACAGATCTTCTTTGATA
GTGTCCATCGATTTCTGGATAACCTGGTTGTCTTTCAGGTTTTCGAACAG
TTTGAAGTAGAAAGAAACGATCTGAGACTG-3'

EqG-5: 5'-GATGATCTTTTTGTCAGAGTCTTCTTTCCAGTTTTTCAGGATGTCCAGGA
ACAGCGGACCACCGTCACCAACGTC-3'

EqG-6: 5'-TGGGTTACGAGCGTTGAAGTATTCTTTCAGGTTTTCGATTTCTTTAAAGA
AAGCAGCCTGCATAAATCACCTCAACCTCTCGAGGGA-3'

50 pMol batches of the oligonucleotides were phosphorylated: EqG-2 together with EqG-5 in 7 mcl, EqG-3 and EqG-8 on their own, each in 8 mcl. The kinase reaction was stopped by heating to 100° C. 50 pMol of EqG-4 (1 mcl) were added to EqG-3 and 50 pMol of EqG-1 (1 mcl) were added to EqG-8. The solutions were heated to 100° C. again and slowly cooled. The solutions of the pairs of oligonucleotides were combined and ligated with T4-DNA ligase in a total of 30 mcl, 2 mcg of pUC18 were doubly cut with EcoRI and HindIII, the vector part was gel-purified and dissolved in 50 mcl of water. 40 ng of vector and about 2 pMol of ligated oligonucleotides were ligated in 10 mcl and the DNA was then transformed into *E. coli* JM101.

The EcoRI-HindIII insert of some resulting plasmids was re-cloned into M13mp9 and the sequence was checked. A plasmid with the expected sequence was selected and designated pGN3.

e) pGN20

About 3 mcg of pGN1 or pGN3, respectively, were doubly cut with HindIII and SalI. The pGN3 insert and the vector/second half of the Eq-γ interferon gene from pGN1 were gel-purified. 0.2 mcg of pGN3 were ligated with about 0.05 mcg of pGN3 insert and the DNA was transformed into *E. coli* JM101. After checking the restriction pattern the plasmid of a resulting clone was selected and designated pGN20.

f) pEqG-QAA2 and pEqG-QAA3

From about 10 mcg of pGN20, the XhoI-EcoRI insert which contains the synthetic horse gamma-interferon gene together with the ribosomal binding site of the *E. coli* enterotoxin II (C. H. Lee et al., Infect. Immun. 42 (1983), 264–268; S. L. Moseley et al., Infect. Immun. 39 (1983), 1167–1174)) was isolated. pRH281/5 or pRH282/5 were doubly cut with XhoI and EcoRI. 20 ng of vector were ligated with 20 ng of insert and the DNA was transformed into *E. coli* HB101. Some colonies were selected, the plasmids were isolated and checked by restriction analysis. One plasmid was selected in each case and designated pEqG-QAA2 (vector: pRH281/5) or pEqG-QAA3 (vector: pRH282/5).

g) Lysate test for interferon-gamma activity

An overnight culture of *E. coli* HB101/pEqG-QAA2 or HB101/pEqG-QAA3 was diluted 1:100 with LB/Amp (LB: 10 g/l tryptone, 5 g/l yeast extract, 5 g/l NaCl, 50 mg/l ampicillin) and incubated further at 37° C. When an optical density (600 nm) of 0.3 was reached, 50 mg/l of indoleacrylic acid were added and the culture was incubated for a further 2 hours at 37° C. The bacteria were separated off by centrifuging and broken up using ultrasound. The sterile filtered supernatant was tested on NBL-6 cells (ATCC CCL 57) for gamma-interferon activity, using vesicular stomatitis virus (VSV) as the virus. The lysates of both transformed bacterial cultures (*E. coli* HB101/pEqG-QAA2 and HB101/pEqG-QAA3) showed about 0.1 to 1 million units/ml of interferon activity. As a control, an identically prepared *E. coli* HB101/pRH281 lysate was tested. This control lysate showed less than 100 units per ml.

We claim:

1. A purified and isolated DNA molecule coding for a polypeptide which has the biological and immunological properties of EqIFN-gamma comprising the following nucleotide sequence, or a degenerate variant thereof:

$R^1$- TAC TGC CAG GCT GCT TTC TTT
AAA GAA ATC GAA AAC CTG AAA
GAA TAC TTC AAC GCT CGT AAC
CCA GAC GTT GGT GAC GGT GGT
CCG CTG TTC CTG GAC ATC CTG
AAA AAC TGG AAA GAA GAC TCT
GAC AAA AAG ATC ATC CAG TCT
CAG ATC GTT TCT TTC TAC TTC
AAA CTG TTC GAA AAC CTG AAA
GAC AAC CAG GTT ATC CAG AAA
TCG ATG GAC ACT ATC AAA GAA
GAT CTG TTC GTT AAA TTC TTC
AAC TCG TCG ACT TCT AAA CTG
GAA GAC TTC CAG AAA CTG ATC
CAG ATC CCA GTT AAC GAC CTG
AAA GTT CAG CGT AAG GCT ATC
TCT GAA CTG ATC AAA GTT ATG
AAC GAC CTG TCT CCA AAA GCT
AAC CTG CGT AAA CGT AAA CGT
TCT CAG AAC CCA TTC CGT GGT
CGT CGT GCT CTT CAG TAA, wherein $R^1$ represents:

ATG AAT TAT ACA AGT TTT ATC

TTG GCT TTT CAG CTG TGT GCG

ATT TTG GGT TCT TCT ACC TAT,

ATG TAT,

TAT,

ATG AAT TAT ACA AGT TTT ATC

TTG GCT TTT CAG CTG TGT GCG

ATT TTG GGT TCT TCT ACC TAC,

ATG TAC, or

TAC.

2. A purified and isolated DNA molecule coding for a polypeptide which has the biological and immunological properties of EqIFN-gamma, comprising of the following nucleotide sequence, or a degenerate variant thereof:

$R^2$-GCT GCT TTC TTT AAA GAA ATC GAA AAC CTG AAA GAA TAC TTC

AAC GCT CGT AAC CCA GAC GTT GGT GAC GGT GGT CCG CTG TTC

CTG GAC ATC CTG AAA AAC TGG AAA GAA GAC TCT GAC AAA AAG

ATC ATC CAG TCT CAG ATC GTT TCT TTC TAC TTC AAA CTG TTC

GAA AAC CTG AAA GAC AAC CAG GTT ATC CAG AAA TCG ATG GAC

ACT ATC AAA GAA GAT CTG TTC GTT AAA TTC TTC AAC TCG TCG

ACT TCT AAA CTG GAA GAC TTC CAG AAA CTG ATC CAG ATC CCA

GTT AAC GAC CTG AAA GTT CAG CGT AAG GCT ATC TCT GAA CTG

ATC AAA GTT ATG AAC GAC CTG TCT CCA AAA GCT AAC CTG CGT

AAA CGT AAA CGT TCT CAG AAC CCA TTC CGT GGT CGT CGT GCT

CTT CAG TAA, wherein $R^2$ represents

ATG AAT TAT ACA AGT TTT ATC TTG GCT TTT CAG CTG TGT GCG ATT TTG GGT TCT

TCT ACC CAG,

ATG CAG, or

CAG.

3. An isolated and purified DNA molecule encoding all or a single contiguous fragment of an EqIFN-γ polypeptide, comprising one or more oligonucleotides selected from the group consisting of:

EG-1, EG-15, or an oligonucleotide degenerate with EG-1 or EG-15, and

EG-3 or an oligonucleotide degenerate therewith, all as shown in FIG. 3;

wherein said oligonucleotides are consecutively linked, 5'→3', in the order recited above.

4. A DNA molecule according to claim 3, further comprising one or more oligonucleotides selected from the group consisting of:

EG-5 or an oligonucleotide degenerate therewith,

EG-7 or an oligonucleotide degenerate therewith,

EG-9 or an oligonucleotide degenerate therewith,

EG-11 or an oligonucleotide degenerate therewith, and

EG-13 or an oligonucleotide degenerate therewith, all as shown in FIG. 3;

wherein said oligonucleotides are consecutively linked, 5'→3', in the order recited above.

5. An isolated and purified DNA molecule encoding all or a single contiguous fragment of an EqIFN-γ polypeptide, comprising one or more oligonucleotides selected from the group consisting of:

EG-7 or an oligonucleotide degenerate therewith,

EG-9 or an oligonucleotide degenerate therewith,

EG-11 or an oligonucleotide degenerate therewith, and

EG-13 or an oligonucleotide degenerate therewith, all as shown in FIG. 3;

wherein said oligonucleotides are consecutively linked, 5'→3', in the order recited above.

6. A DNA molecule according to claim 5, further comprising, 3' to said one or more oligonucleotides, an additional one or more oligonucleotides selected from the group consisting of:

EG-1, EG-15, or an oligonucleotide degenerate with EG-1 or EG-15,

EG-3 or an oligonucleotide degenerate therewith, and

EG-5 or an oligonucleotide degenerate therewith, all as shown in FIG. 3;

wherein said additional oligonucleotides are consecutively linked, 5'→3', in the order recited above.

7. An expression vector comprising the isolated and purified DNA molecule of any one of claims 1–6.

8. A transformed host cell comprising the expression vector of claim 7.

9. The transformed host cell of claim 8 which is *Escherichia coli.*

10. A process for preparing all or a fragment of an EqIFN-γ polypeptide, comprising a) culturing the transformed host cell of claim 8;

b) causing said host cell to express said polypeptide; and c) isolating said polypeptide.

11. The purified and isolated DNA molecule of claim 1 or 2, further comprising an expression control sequence which is functionally linked to said DNA molecule.

12. The isolated and purified DNA molecule of claim 11, wherein said expression control sequence is a modified trp promoter from *Serratia marcescens.*

13. An expression vector comprising the isolated and purified DNA molecule of claim 12.

14. A transformed host cell comprising the expression vector of claim 13.

15. The transformed host cell of claim 14 which is *Escherichia coli.*

16. A process for preparing a polypeptide with the biological and immunological properties of EqIFN-γ, comprising a) culturing the transformed host cell of claim 14;

b) causing said host cell to express said polypeptide; and c) isolating said polypeptide.

17. The isolated and purified DNA molecule of claim 12, wherein said expression control sequence is selected from the group consisting of the following DNA molecules:

GAATTGACGC TGATCGCTAA AACATTGTGC AAAAAGAGGG TTGACATTGC 50

CTTCGCGAAC CAGTTAACTA GTACACAAGT TCACGGCTCG AGACGGTAAG 100

GAGGTTTAAT ATGAGCTCGA ATTCATCGAT, and

GAATTGCCCG TTCTGGATAA TGTTTTTTGC GCCGACATCA TCATGCTGAT 50

CGCTAAAACA TTGTGCAAAA AGAGGGTTGA CATTGCCTTC GCGAACCAGT 100

TAACTAGTAC ACAAGTTCAC GGCTCGAGAC GGTAAGGAGG TTTAATATGA 150

GCTCGAATTC ATCGAT.

18. An expression vector comprising the isolated and purified DNA molecule of claim 17.

19. A transformed host cell comprising the expression vector of claim 18.

20. The transformed host cell of claim 19 which is *Escherichia coli.*

21. A process for preparing a polypeptide with the biological and immunological properties of EqIFN-γ, comprising a) culturing the transformed host cell of claim 19;

b) causing said host cell to express said polypeptide; and c) isolating said polypeptide.

* * * * *